United States Patent [19]
Ryan et al.

[11] Patent Number: 5,350,411
[45] Date of Patent: Sep. 27, 1994

[54] PACEMAKER TELEMETRY SYSTEM

[75] Inventors: Terrence G. Ryan, North Oaks; James W. Busacker, Buffalo; Robert A. Hochban, Circle Pines, all of Minn.

[73] Assignee: Medtronic, Inc., Minneapolis, Minn.

[21] Appl. No.: 85,489

[22] Filed: Jun. 28, 1993

[51] Int. Cl.$^5$ .............................................. A61N 1/02
[52] U.S. Cl. ........................................ 607/32; 607/60
[58] Field of Search ............................ 607/31, 32, 60; 128/903

[56] References Cited

U.S. PATENT DOCUMENTS

| | | | |
|---|---|---|---|
| 3,833,005 | 9/1974 | Wingrott | 607/31 |
| 4,124,031 | 11/1978 | Mensink et al. | 607/31 |
| 4,531,523 | 7/1985 | Anderson | 128/903 |
| 4,561,443 | 12/1985 | Hogreff et al. | 607/32 |
| 4,592,360 | 6/1986 | Lesnick | 607/60 |
| 5,052,389 | 10/1991 | Henry | 607/32 |
| 5,241,967 | 9/1993 | Henry | 607/32 |

FOREIGN PATENT DOCUMENTS 9111063 7/1991 PCT Int'l Appl. .............. 607/32

*Primary Examiner*—William E. Kamm
*Attorney, Agent, or Firm*—Gregory P. Gadson; Harold R. Patton

[57] ABSTRACT

An implantable medical device telemetry system provides a means for decoding telemetry downlink information transmitted from an external unit to an implanted medical device, and for encoding telemetry uplink signals to be transmitted from the implanted device to the external unit. A novel system architecture results in a very small telemetry subsystem in the implanted device and a very flexible system adaptable to be used in conjunction with various telemetry formats of various implanted devices. A programmable logic array (PLA) structure that is mask programmable and which may further be partially RAM programmable serves as the basis of the telemetry subsystem. For downlink telemetry, a counter is enabled during intervals of interest in the downlink RF burst stream. The counter value at the end of such an interval is then applied to the variable inputs of the PLA tier decoding in accordance with a selected telemetry protocol. For uplink telemetry, the counter and PLA is used to control transmission of uplink telemetry pulses, such that pulses are pulse-position modulated in accordance with data to be transmitted. Various different telemetry protocols may be supported by the same telemetry circuit, which may be mask-programmed at the time of manufacture to be compatible with one or more different telemetry protocols.

27 Claims, 10 Drawing Sheets

PACEMAKER TELEMETRY SYSTEM

FIELD OF THE INVENTION

This invention relates to the field of implantable medical devices, and more particularly relates to implantable medical device systems which include a telemetry subsystem.

BACKGROUND OF THE INVENTION

Since the introduction of the first implantable pacemakers in the 1960's, there have been considerable advancements both in the field of electronics and the field of medicine, such that there is presently a wide assortment of commercially-available implantable medical devices. The class of implantable medical devices now includes not only pacemakers, but also implantable cardioverters, defibrillators, neural stimulators, and drug administering devices. Today's state-of-the-art implantable medical devices are vastly more sophisticated and complex than early pacemakers, capable of performing significantly more complex tasks. The therapeutic benefits of such devices have been well-proven.

As the functional sophistication and complexity of implantable medical devices has increased over the years, it has become increasingly more important for such devices to be equipped with a telemetry system for enabling them to communicate with an external unit.

For example, shortly after the introduction of the earliest fixed-rate, noninhibited pacemakers, it became apparent that it would be desirable for a physician to non-invasively exercise at least some amount of control over the device, e.g., to turn the device on or off or adjust the fixed pacing rate, after implant. In early devices, one way the the physician was able to have some control over implantable device operation was through the provision of a magnetic reed switch in the implantable device. After implant, the reed switch would be actuated by placing a magnet over the implant site. Reed switch closure could then be used, for example, to alternately activate or deactivate the device. Alternatively, the fixed pacing rate of the device could be adjusted up or down by incremental amounts based upon the duration of reed switch closure. Many different schemes utilizing a reed switch to adjust parameters of implanted medical devices have been developed. See, for example, U.S. Pat. No. 3,311,111 to Bowers, U.S. Pat. No. 3,518,997 to Sessions, U.S. Pat. No. 3,623,486 to Berkovits, U.S. Pat. No. 3,631,860 to Lopin, U.S. Pat. No. 3,738,369 to Adams et al., U.S. Pat. No. 3,805,796 to Terry, Jr., and U.S. Pat. No. 4,066,086 to Alferness et al.

As new, more advanced features are incorporated into implantable devices, it is typically necessary to convey correspondingly more information to the device relating to the selection and control of those features. For example, if a pacemaker is selectively operable in various pacing modes (e.g., VVI, VDD, DDD, etc. . . ), it is desirable that the physician or clinician be able to non-invasively select a mode of operation. Similarly, if the pacemaker is capable of pacing at various rates, or of delivering stimulating pulses of varying energy levels, it is desirable that the physician or clinician be able to select, on a patient-by-patient basis, appropriate values for such variable operational parameters.

Even greater demands are placed upon the telemetry system in implantable devices having such advanced features as rate adaptation based upon activity sensing, as disclosed, for example, in U.S. Pat. No. 5,052,388 to Sivula et al. entitled "Method and Apparatus for Implementing Activity Sensing in a Pulse Generator", in U.S. patent application Ser. No. 07/567,372 in the name of Sivula, et al. entitled "Rate Responsive Pacemaker and Method for Automatically Initializing the Same" [The "Duet auto-init" application], and in U.S. patent application Ser. No. 07/880,877 in the name of Shelton et al., entitled "Work-Modulated Pacing Rate Deceleration". The Sivula et al. '388 patent and the Sivula 07/567,372 and Shelton et al. 07/880,877 applications are each hereby incorporated by reference herein in their entireties.

The information which must be communicated to the implantable device in today's state-of-the-art pacemakers includes: pacing mode, multiple rate response settings, electrode polarity, maximum and minimum pacing rates, output energy (output pulse width and/or output current), sense amplifier sensitivity, refractory periods, calibration information, rate response attack (acceleration) and decay (deceleration), onset detection criteria, and perhaps many other parameter settings.

The need to be able to communicate more and more information to implanted devices quickly rendered the simple reed-switch closure arrangement insufficient. Also, it has become apparent that it would also be desirable not only to allow information to be communicated to the implanted device, but also to enable the implanted device to communicate information to the outside world.

For diagnostic purposes, for example, it is desirable for the implanted device to be able to communicate information regarding its operational status to the physician or clinician. State of the art implantable devices are available which can even transmit a digitized ECG signal for display, storage, and/or analysis by an external device.

As used herein, the terms "uplink" and "uplink telemetry" will be used to denote the communications channel for conveying information from the implanted device to an external unit of some sort. Conversely, the terms "downlink" and "downlink telemetry" will be used to denote the communications channel for conveying information from an external unit to the implanted device.

Various telemetry systems for providing the necessary communications channels between an external unit and an implanted device have been shown in the art. Telemetry systems are disclosed, for example, in the following U.S. Patents: U.S. Pat. No. 4,539,992 to Calfee et al. entitled "Method and Apparatus for Communicating With Implanted Body Function Stimulator"; U.S. Pat. No. 4,550,732 to Batty Jr. et al. entitled "System and Process for Enabling a Predefined Function Within An Implanted Device"; U.S. Pat. No. 4,571,589 to Slocum et al. entitled "Biomedical Implant With High Speed, Low Power Two-Way Telemetry"; U.S. Pat. No. 4,676,248 to Berntson entitled "Circuit for Controlling a Receiver in an Implanted Device"; U.S. Pat. No. 5,127,404 to Wyborny et al. entitled "Telemetry Format for Implanted Medical Device"; U.S. Patent No. 4,211,235 to Keller, Jr. et al. entitled "Programmer for Implanted Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above-referenced patents are employed in conjunction with an external programming/processing unit. One programmer for non-invasively programming a cardiac pacemaker is described in its various aspects in the following U.S. Patents to Hartlaub et al., each commonly assigned to the assignee of the present invention and each incorporated by reference herein: U.S. Pat. No. 4,250,884 entitled "Apparatus For and Method Of Programming the Minimum Energy Threshold for Pacing Pulses to be Applied to a Patient's Heart"; U.S. Pat. No. 4,273,132 entitled "Digital Cardiac Pacemaker with Threshold Margin Check"; U.S. Pat. No. 4,273,133 entitled "Programmable Digital Cardiac Pacemaker with Means to Override Effects of Reed Switch Closure"; U.S. Pat. No. 4,233,985 entitled "Multi-Mode Programmable Digital Cardiac Pacemaker"; and U.S. Pat. No. 4,253,466 entitled "Temporary and Permanent Programmable Digital Cardiac Pacemaker".

Aspects of the programmer that is the subject of the foregoing Hartlaub et al. patents (hereinafter "the Hartlaub programmer") are also described in U.S. Pat. No. 4,208,008 to Smith, entitled "Pacing Generator Programing Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

Although various different telemetry systems have been employed in the prior art, the present inventors believe that there remains a need for a telemetry system which is small and consumes relatively little power, both being extremely critical considerations in the context of battery-powered implantable medical devices. Many of the known telemetry systems (see, e.g., the above-referenced Calfee et al., Batty, Jr. et al., and Slocum et al. patents) are implemented with complex, energy-consuming circuits. Moreover, known telemetry systems are often implemented in hardwired, nonflexible circuitry not readily adaptable to more than one telemetry protocol.

Additionally, the very existence of so many different telemetry systems can itself be problematic, since even different devices from the same manufacturer may employ different and incompatible telemetry systems. From both a marketing standpoint and a manufacturing standpoint, it is costly and inefficient to require different programmers for each different device made by a given manufacturer.

For a given device, the uplink and downlink telemetry protocols may be entirely different and incompatible, since considerations of energy consumption and efficiency are different for an implanted device than for an external programming/control unit. From energy consumption and device cost standpoints, the need for two different telemetry circuits in an implanted device is clearly undesirable.

SUMMARY OF THE INVENTION

The present invention, therefore, relates to a telemetry system particularly well-suited for inclusion in a battery-powered implantable medical device.

In accordance with one aspect of the present invention, a telemetry system is provided both for decoding downlink telemetry signals and encoding uplink telemetry signals. The flexible circuit architecture in accordance with the present invention is small and consumes a relatively small amount of power. The flexibility of the architecture enables the same telemetry circuit to be utilized for both uplink and downlink telemetry, and allows the circuit to be readily adapted for use with a variety of different telemetry protocols.

In accordance with an embodiment of the invention to be described herein, an RF telemetry signal are received by an antenna in an implantable medical device. The RF signal comprises a sequence of high-frequency pulses or bursts. The disclosed embodiment uses pulse interval modulation to encode downlink telemetry data, wherein the interval between trailing edges of RF bursts in the telemetry signal is modulated according to the digital data to be transmitted to the implanted device. In particular, a shorter interval is interpreted as a "0" bit, and a longer interval is interpreted as a "1" bit. In accordance with one feature of the present invention, however, it is believed that the telemetry system is readily adaptable to different types of telemetry encoding schemes, and may therefore be advantageously practiced in telemetry systems not employing pulse interval modulation.

In the telemetry system in accordance with the present invention, the sequence of RF bursts in the downlink telemetry signal are converted to a sequence of square wave pulses in a conventional manner. The square wave pulses are then applied to a novel circuit which includes a programmable logic array (PLA) that is maskprogrammable and which may also be partially RAM programmable. The PLA serves as a central part of the system.

For downlink telemetry, a counter is used to provide a measure of various time intervals of interest (e.g., trailing-edge to trailing-edge intervals, pulse width intervals, etc . . . ) in the downlink telemetry signal. The output from the counter is applied to the variable inputs of the PLA. When a match between a counter value presented to the PLA and a first programmed term of the PLA, a "0" bit is shifted into a shift register in the telemetry circuit. When a match between a counter value and another programmed term of the PLA, a "1" is shifted into the shift register. Thus, different downlink telemetry protocols may be supported by a programmer incorporating a telemetry system in accordance with the present invention, either by providing an appropriate PLA for a given protocol, or by providing programming for multiple protocols in a single PLA.

For uplink telemetry in one of the disclosed embodiments, data is pulseposition encoded. The counter in the telemetry system is used to define a plurality of time slots in an uplink telemetry frame. The PLA in the telemetry is programmed such that when a match between a counter value and data to be transmitted occurs, an RF uplink telemetry pulse is produced. In this way, a pulse in produced at a position within the uplink telemetry frame which is proportional to the data value to be transmitted.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF SPECIFIC EMBODIMENTS OF THE INVENTION

Figure 1:
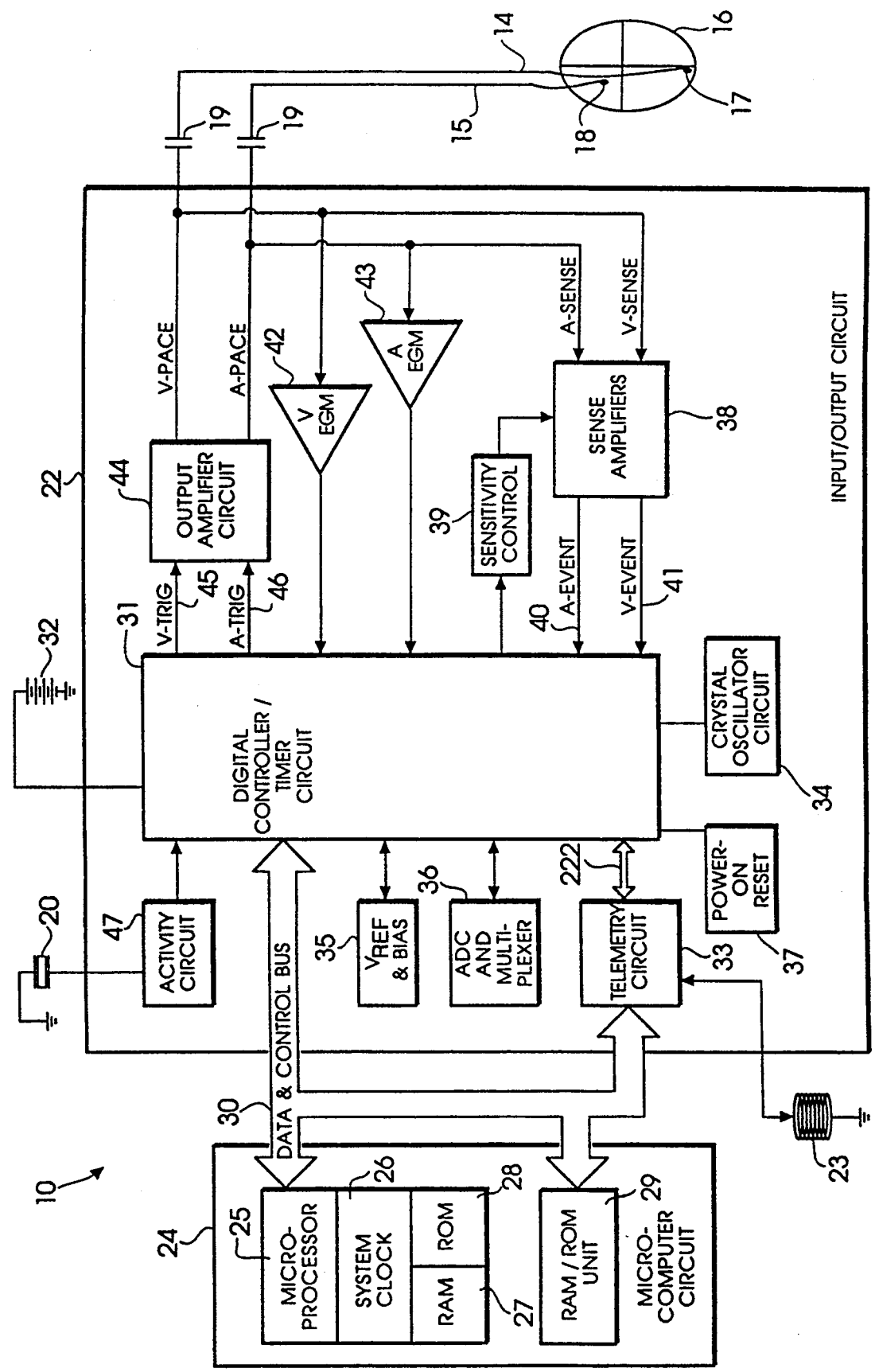
FIG. 1 is a block diagram of an implantable pacemaker incorporating a telemetry subsystem in accordance with one embodiment of the invention.

Referring to FIG. 1, there is shown a block diagram of an implantable pacemaker 10 which incorporates a telemetry subsystem in accordance with the present invention. Although the present invention will be described herein in conjunction with a pacemaker 10 having a microprocessor-based architecture, it will be understood that pacemaker 10 may be implemented in any logic based, custom integrated circuit architecture, if desired. The pacemaker shown in FIG. 1 is substantially similar to that disclosed in co-pending U.S. patent application Ser. No. 07/794,766 filed by Paul Stein and entitled "Method and Apparatus for Implementing Activity Sensing in a Pulse Generator", and in co-pending U.S. patent application Ser. No. 07/870,062 filed by Wahlstrand et al. entitled "Method and Apparatus for Rate-Responsive Cardiac Pacing". The Stein 07/794,766 and Wahlstrand 07/870,062 applications are each hereby incorporated herein by reference in their entireties.

Although a particular implementation of a pacemaker is disclosed herein, it is to be understood that the present invention may be advantageously practiced in conjunction with many different types of pacemakers, such as the pacemaker described in the abovereferenced Sivula et al. patent, for example, as well as other types of implantable medical devices.

In FIG. 1, pacemaker 10 is shown to include an activity sensor 20, which may be, for example, a piezoelectric element bonded to the inside of the pacemaker's shield. Such a pacemaker/activity sensor configuration is the subject of the above-referenced patent to Anderson et al. Piezoelectric sensor 20 provides a sensor output which varies as a function of a measured parameter that relates to the metabolic requirements of a patient.

Pacemaker 10 of FIG. 1 is programmable by means of an external programming unit (not shown in FIG. 1). One such programmer suitable for the purposes of the present invention is the Medtronic Model 9760 programmer which is commercially available and is intended to be used with all Medtronic pacemakers. The 9760 programmer is a microprocessor-based device which provides a series of encoded signals to pacemaker 10 by means of a programming head which transmits radio-frequency (RF) encoded signals to pacemaker 10 according to the telemetry system laid out, for example, in U.S. Pat. No. 5,127,404 to Wyborny et al. entitled "Improved Telemetry Format", which is assigned to the assignee of the present invention and which is incorporated herein by reference in its entirety. It is to be understood, however, that the programming methodology disclosed in the above-referenced patent is identified herein for the purposes of illustration only, and that any programming methodology may be employed so long as the desired information can be conveyed between the pacemaker and the external programmer.

It is believed that one of skill in the art would be able to choose from any of a number of available pacemaker programmers and programming techniques to accomplish the tasks necessary for practicing the present invention. As noted above, however, the Medtronic Model 9760 programmer is presently preferred by the inventors.

In the illustrative embodiment of the present invention, parameters such as the lower rate of pacemaker 10 may be programmable, for example from 40 to 90 pulses per minute (PPM) in increments of 10 PPM, and the upper rate may be programmable, for example, between 100 and 175 PPM in 25 PPM increments. There may also be programmable rate response functions in pacemaker 10.

Pacemaker 10 is schematically shown in FIG. 1 to be electrically coupled via pacing lead 14 and 15 to a patient's heart 16. Leads 14 and 15 include one or more intracardiac electrodes, designated as 17 and 18 in FIG. 1, located near their distal ends of leads 14 and 15, respectively, and positioned within the right ventricular (RV) and right atrial (RA) chambers, respectively, of heart 16. Leads 14 and 15 can be of either the unipolar or bipolar type as is well known in the art; alternatively, a single, multiple-electrode lead may be used.

Electrodes 17 and 18 are coupled via suitable lead conductors through input capacitors 19 to input/output terminals of an input/output circuit 22. In the presently disclosed embodiment, activity sensor 20 is bonded to the inside of the pacemaker's outer protective shield, in accordance with common practice in the art. As shown in FIG. 1, the output from activity sensor 20 is also coupled to input/output circuit 22.

Input/output circuit 22 contains the analog circuits for interface to the heart 16, activity sensor 20, an antenna 23, as well as circuits for the application of stimulating pulses to heart 16 to control its rate as a function thereof under control of the software-implemented algorithms in a microcomputer circuit 24.

Microcomputer circuit 24 comprises a microprocessor 25 having an internal system clock circuit 26, and on-board RAM 27 and ROM 28. Microcomputer circuit 24 further comprises a RAM/ROM unit 29. Microprocessor 25 and RAM/ROM unit 29 are each coupled by a data and control bus 30 to a digital controller/timer circuit 31 within input/output circuit 22. Microcomputer circuit 24 may be a commercially-available, general-purpose microprocessor or microcontroller, or may be a custom integrated circuit device augmented by standard RAM/ROM components.

It will be understood that each of the electrical components represented in FIG. 1 is powered by an appropriate implantable battery power source 32, in accordance with common practice in the art. For the sake of clarity, the coupling of battery power to the various components of pacemaker 10 has not been shown in the Figures.

An antenna 23 is connected to input/output circuit 22 for purposes of uplink/downlink telemetry through an RF telemetry circuit 33 in accordance with one embodiment of the invention, to be hereinafter described in greater detail. In the embodiment of FIG. 1, telemetry circuit 33 is coupled to digital controller/timer circuit 31. It is contemplated that telemetry circuit 33 may also be coupled directly to microcomputer circuit 24 via data and control bus 30.

A crystal oscillator circuit 34, typically a 32,768 Hz crystal-controlled oscillator, provides main timing clock signals to digital controller/timer circuit 31. A $V_{REF}$ and Bias circuit 35 generates stable voltage reference and bias currents for the analog circuits of input-/output circuit 22. An analog-to-digital converter (ADC) and multiplexer unit 36 digitizes analog signals and voltages to provide "real-time" telemetry intracardiac signals and battery end-of-life (EOL) replacement function. A power-on-reset (POR) circuit 37 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 30 to digital controller/timer circuit 31 wherein digital timers and counters are employed to establish the overall escape interval of the pacemaker, as well as various refractory, blanking, and other timing windows for controlling the operation of the peripheral components within input-/output circuit 22.

Digital controller/timer circuit 31 is coupled to sensing circuitry including a sense amplifier circuit 38 and a sensitivity control circuit 39. In particular, digital controller/timer circuit 31 receives an A-EVENT (atrial event) signal on line 40, and a V-EVENT (ventricular event) signal on line 41. Sense amplifier circuit 38 is coupled to leads 14 and 15, in order to receive the V-SENSE (ventricular sense) and A-SENSE (atrial sense) signals from heart 16. Sense amplifier circuit 38 asserts the A-EVENT signal on line 40 when an atrial event (i.e., a paced or intrinsic atrial event) is detected, and asserts the V-EVENT signal on line 41 when a ventricular event (paced or intrinsic) is detected. Sense amplifier circuit 38 includes one or more sense amplifiers corresponding, for example, to that disclosed in U.S. Pat. No. 4,379,459 issued to Stein on Apr. 12, 1983, incorporated by reference herein in its entirety.

Sensitivity control 39 is provided to adjust the gain of sense amplifier circuitry 38 in accordance with programmed sensitivity settings, as would be appreciated by those of ordinary skill in the pacing art.

A V-EGM (ventricular electrocardiogram) amplifier 42 is coupled to lead 14 to receive the V-SENSE signal from heart 16. Similarly, an A-EGM (atrial electrocardiogram) amplifier 43 is coupled to lead 15 to receive the A-SENSE signal from heart 16. The electrogram signals developed by V-EGM amplifier 42 and A-EGM amplifier 43 are used on those occasions when the implanted device is being interrogated by external programmer 11, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference.

Digital controller and timer circuit 31 is coupled to an output amplifier circuit 44 via two lines 45 and 46, designated V-TRIG (ventricular trigger) and A-TRIG (atrial trigger), respectively. Circuit 31 asserts the V-TRIG signal on line 45 in order to initiate the delivery of a ventricular stimulating pulse to heart 16 via pace/-sense lead 14. Likewise, circuit 31 asserts the A-TRIG signal on line 46 to initiate delivery of an atrial stimulating pulse to heart 16 via pace/sense lead 15. Output amplifier circuit 44 provides a ventricular pacing pulse (V-PACE) to the right ventricle of heart 16 in response to the V-TRIG signal developed by digital controller/timer circuit 31 each time the ventricular escape interval times out, or an externally transmitted pacing command has been received, or in response to other stored commands as is well known in the pacing art. Similarly, output amplifier circuit 44 provides an atrial pacing pulse (A-PACE) to the right atrium of heart 16 in response to the A-TRIG signal developed by digital controller/timer circuit 31. Output amplifier circuit 44 includes one or more output amplifiers which may correspond generally to that disclosed in U.S. Pat. No. 4,476,868 issued to Thompson on Oct. 16, 1984 also incorporated herein by reference in its entirety.

As would be appreciated by those of ordinary skill in the art, input/output circuitry will include decoupling circuitry for temporarily decoupling sense amplifier circuit 38, V-EGM amplifier 45 and A-EGM amplifier 46 from leads 14 and 15 when stimulating pulses are being delivered by output amplifier circuit 44. For the sake of clarity, such decoupling circuitry is not depicted in FIG. 2.

While specific embodiments of sense amplifier circuitry, output amplifier circuitry, and EGM amplifier circuitry have been identified herein, this is done for the purposes of illustration only. It is believed by the inventor that the specific embodiments of such circuits are not critical to the present invention so long as they provide means for generating a stimulating pulse and provide digital controller/timer circuit 31 with signals indicative of natural and/or stimulated contractions of the heart. It is also believed that those of ordinary skill in the art could chose from among the various well-known implementations of such circuits in practicing the present invention.

Digital controller/timer circuit 31 is coupled to an activity circuit 47 for receiving, processing, and amplifying activity signals received from activity sensor 20. A suitable implementation of activity circuit 47 is described in detail in the above-referenced Sivula et al. application. It is believed that the particular implementation of activity circuit 47 is not critical to an understanding of the present invention, and that various activity circuits are well-known to those of ordinary skill in the pacing art.

Figure 2:
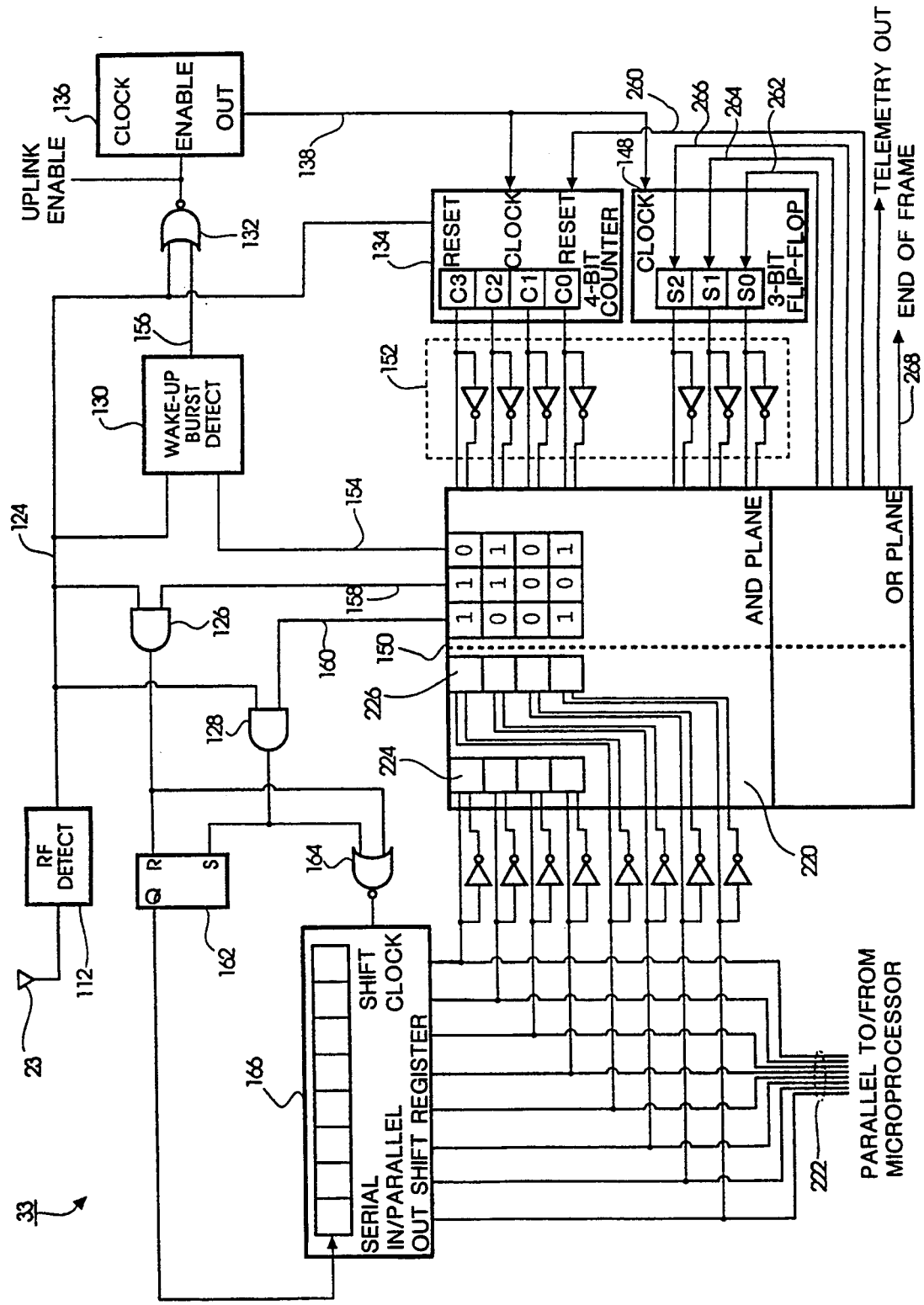
FIG. 2 is a block diagram of the telemetry system in the pacemaker of FIG. 1.

Referring to FIG. 2, there is shown a block diagram of radio-frequency (RF) telemetry subsystem 33 in accordance with one embodiment of the present invention. Telemetry subsystem 33 of FIG. 2 is coupled to antenna 23, as previously noted, for receiving RF signals from an external programming unit (not shown in the Figures) such as the Model 9760 Programmer available from Mealtronic, Inc., Minneapolis, Minn.

In the presently preferred embodiment of the invention, the external programmer transmits signals in the form of a series of short RF pulses. In accordance with one aspect of the present invention to be hereinafter described in greater detail, telemetry system 33 of FIG. 2 is capable of being readily adapted for use in a variety of different telemetry schemes involving streams of RF pulses. In particular, it is believed the the telemetry system of FIG. 1 may be utilized in pulse position modulation, pulse width modulation, pulse interval modulation, and other types of telemetry protocols. In one embodiment to be described herein in some detail, it will be assumed that a pulse interval modulation scheme will be supported, wherein the circuit of FIG. 1 distinguishes between "0" data and "1" data based upon the duration of time intervals between successive pulses received by antenna 10. However, it is believed by the inventors that those of ordinary skill in the art having the benefit of the present disclosure will be readily able to adapt the present invention to be used in support of other types of telemetry schemes, particularly those based upon some form of pulse modulation.

As noted above, there are various pulse modulation schemes that may be employed for the purposes of downlink telemetry. In one, called pulse interval modulation, binary information is encoded such that the duration of the interval between RF bursts in the telemetry downlink signal is used to indicate the type of data (i.e., a zero or a one). In a variation of pulse interval modulation, the duration of the interval between successive trailing edges of RF bursts in the downlink signal encodes the data.

Figure 3:
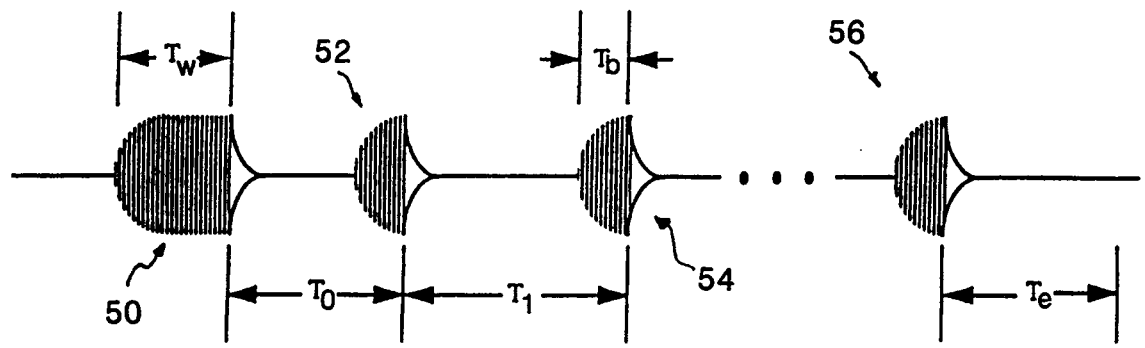
FIG. 3 is an illustration of an RF telemetry downlink signal waveform.

The various downlink telemetry encoding protocols to be described herein will perhaps best be appreciated with reference to FIG. 3, which shows a portion of one type of pulse interval modulated RF signal that may be received by antenna 10.

The RF signal of FIG. 3 consists of a stream of pulses of a 175 kHz ($\pm 6$ kHz) sinusoidal RF signal. In FIG. 3, a first RF pulse, designated generally as 50, is called a "wake-up" or "start-of-message" burst, and has a duration of $T_w = 2000$ $\mu$Sec$\pm 30$ $\mu$Sec. The wake-up burst 40 is issued to inform the telemetry circuitry that new data is to follow. Also shown in FIG. 3 are a number of "data bursts" designated generally as 52, 54, and 56.

In accordance with one telemetry protocol supported by the presently disclosed embodiment of the invention, the telemetry circuitry must recognize any burst within the range specified above for $T_w$ (i.e., any burst with duration between 1970 $\mu$Sec and 2030 $\mu$Sec) as a start-of-message, unless such burst appears during a downlink message (i.e., from the time the telemetry circuit first recognizes a start-of-message burst until it recognizes an end-of-message burst, to be hereinafter described).

A message from the external unit is terminated with an "end-of-message" indicator, which comprises an interval $T_c$ between any two consecutive trailing edges of greater than 2440 $\mu$Sec. Thus, once the telemetry circuit has recognized a start-of-message burst, any pause between trailing edges of consecutive pulses which exceeds 2440 $\mu$Sec is recognized as an end-of-message indicator.

All downlink telemetry transmissions consists of a start-of-message burst followed by a number of data bursts, where the time between trailing edges of data bursts indicates either a "0" bit or a "1" bit. Alternatively, the time between the trailing edge of one burst and the rising edge of the next burst can be used to encode the data.

In FIG. 3, the interval between the trailing edge of start-of-message burst 50 and the trailing edge of data burst 52 is designated as $T_0$. The time interval between the trailing edge of data burst 42 and the trailing edge of data burst 54 is designated as $T_1$. The telemetry circuit in accordance with one embodiment of the invention interprets the intervals between trailing edges as follows: if the interval between trailing edges is in the range 900 $\mu$Sec$\pm 30$ $\mu$Sec, this is interpreted as a "0" bit; similarly, if the range is in the range 2,200 $\mu$Sec$\pm 30$ $\mu$Sec, this is interpreted as a "1" bit.

Each data burst (such as 52, 54, and 56) in FIG. 3 is specified to have a duration of 200 $\mu$Sec$\pm 50$ $\mu$Sec. As would be appreciated by those of ordinary skill in the art, if the duration of data bursts is known and consistent, then the above-described two types of pulse interval modulation (i.e., trailing-edge to trailing-edge and trailing-edge to rising-edge) can be successfully demodulated by detecting and measuring the intervals between the trailing edge of one pulse and the rising edge of the next.

For the embodiment of the present invention shown in FIG. 2, it will be assumed that the above-described trailing-edge to trailing-edge pulse interval modulation scheme is used for downlink telemetry. However, as will be apparent to those of ordinary skill in the art, the system of FIG. 2 to be hereinafter described in greater detail demodulates the pulse stream of FIG. 3 on a trailing-edge to rising-edge basis.

Figure 4:
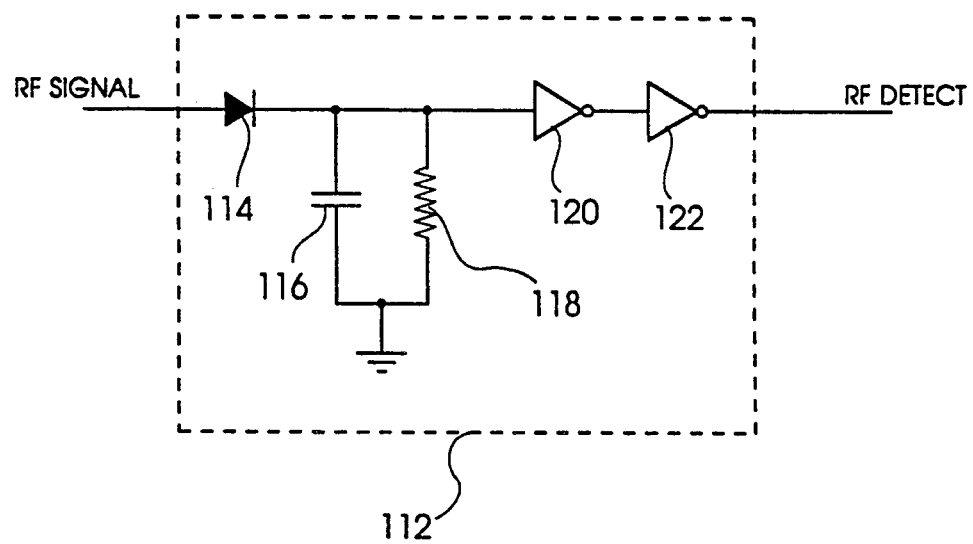
FIG. 4 is a schematic diagram of the RF detect circuit in the telemetry system of FIG. 2.

Signals consisting of a stream of RF bursts such as are depicted in FIG. 3 are received by antenna 23 in the circuit of FIG. 2, and are applied to an RF detect circuit 112 which converts the RF pulses in the antenna signal to positive logic square-wave pulses, in a conventional manner. In particular, RF detect circuit 112 may be as illustrated in the schematic diagram of FIG. 4, comprising a diode 114, a capacitor 116 and resistor 118 coupled in parallel to ground, and two inverters 120 and 122. As would be appreciated by those of ordinary skill in the art, circuit 112 operates to produce a square-wave digital pulse output signal with positive-going pulses corresponding to RF bursts in the received RF signal.

The square-wave digital pulse stream output signal derived by detect circuit 112 is conveyed on line 124 to one input of an AND gate 126, one input of a second AND gate 128, one input of a wake-up burst detect circuit 130, and one input of a NOR gate 132. The signal on line 124 is also applied to the RESET input of an N-bit counter 134.

Wake-up burst detect circuit functions to de-assert its output signal on line 156 upon detection of an RF burst of sufficient duration to qualify as a wake-up burst according to the protocol described above with reference to FIG. 3. The output signal on line 156 from wake-up burst detector 130 is applied to a second input of NOR gate 132.

The output of NOR gate 132 is applied to the ENABLE input of a clock circuit 136. Clock circuit 136 is enabled by a high logic level signal applied to its ENABLE input and, when enabled, produces a 4 kHz clock signal on line 138. The clock signal on line 138 is applied to the clock inputs of N-bit counter 134, and to the clock input of an M-bit flip-flop array 148.

In accordance with an important aspect of the present invention, telemetry circuit 33 of FIG. 2 also includes a programmable logic array (PLA) 150. As would be appreciated by those of ordinary skill in the art, a PLA is an array of switching elements that can be programmed to allow implementation of sum-of-products expressions. In general, a PLA has a plurality of input variables and a plurality of output variables. Each function is realized as a sum of product terms involving the input variables. The variables are presented to a PLA in true and complemented form to an AND array in the PLA, where a plurality of product terms are formed. These are then gated to an OR array in the PLA, where the output functions are formed. In the circuit of FIG. 2, the variables applied to PLA 150 are supplied from N-bit counter 134 and from M-bit flip-flop array 148. As shown in FIG. 2, each of the output signals from counter 134 and flip-flop array 148 are applied to an inverter array 152 so that both true and complemented forms of the signals can be supplied to PLA 150. PLA 150 is programmed such that certain combinations of input signals cause corresponding output signals to be asserted.

One of the output lines from PLA 150, designated as 154 in FIG. 2, is applied to a second input of wake-up detector circuit 130. When the signal from PAL 150 on line 154 is asserted, this causes wake-up detector circuit 130 to assert its output signal on line 156, such that the output from NOR gate 132 is deasserted, thereby disabling clock 136.

Another of the output lines from PLA 150, designated as 158 in FIG. 1, is applied to a second input of AND gate 126. Yet another of the output lines from PLA 150, designated as 160, is applied to a second input of AND gate 128.

The output of AND gate 126 is applied to a "reset" (R) input of an RS flip-flop 162, while the output from AND gate 128 is applied to the "set" (S) input of flip-flop 162. The output from AND gates 126 and 128 are also each applied to an input of a NOR gate 164. The output from NOR gate 164 is applied to the SHIFT CLOCK input of an eight-bit serial-in/parallel-out shift register 166. The output (Q) from RS flip-flop 162 is applied to the shift data input to shift register 166.

Operation of the circuit of FIG. 2 as thus far described will perhaps best be explained with reference to the timing diagram of FIG. 5.

Figure 5:
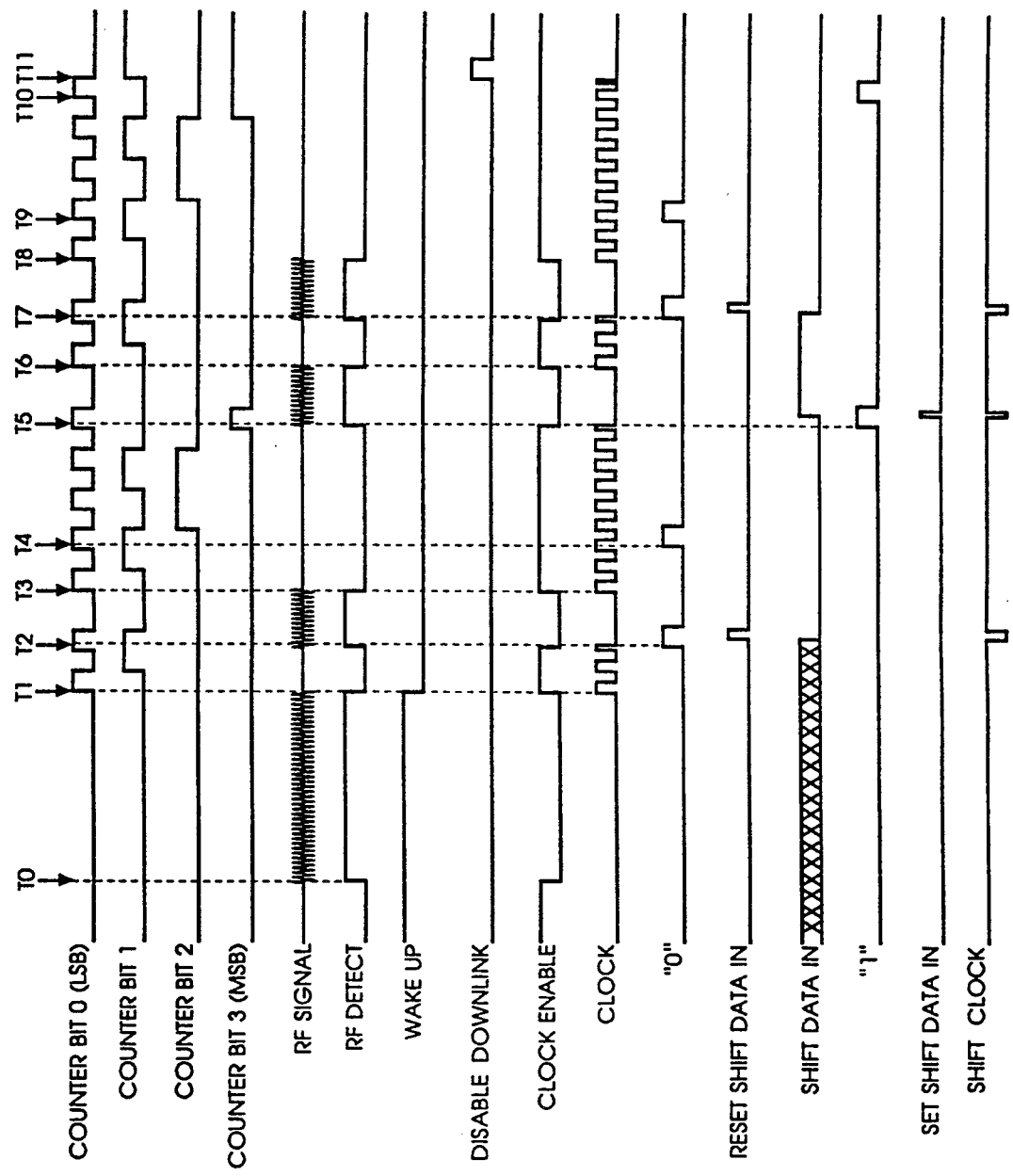
FIG. 5 is a timing diagram illustrating the time relationship between signals present in the telemetry system of FIG. 2.

In FIG. 5, the binary value appearing at the outputs of counter 134 are represented by the waveforms COUNTER BIT 0 (LSB), COUNTER BIT 1, COUNTER BIT 2, and COUNTER BIT 3 (MSB). These values are applied via inverter array 152 to the variable inputs of PLA 150. The waveform designated RF SIGNAL in FIG. 5 represents the RF signal received by antenna 23 in the circuit of FIG. 1. The waveform designated RF DETECT represents the output of RF detect circuit 112, which waveform is present on line 124 in FIG. 2. The waveform WAKE UP in FIG. 5 represents the output of wake-up burst detector circuit 130, which is applied to one input of NOR gate 132 on line 156. The waveform CLOCK ENABLE in FIG. 5 represents the output of NOR gate 132; when asserted, this signal enables clock 136. The waveform DISABLE DOWNLINK represents the output on line 154 from PLA 150; when asserted, (i.e., at a high logic level), the output from NOR gate 132 is prevented from going to a high logic level, thus preventing clock 136 from being enabled. The waveforms "0" and "1" in FIG. 5 represent the output signals on lines 160 and 158, respectively, from PLA 150. The waveform RESET SHIFT DATA IN represents the output from AND gate 126 in FIG. 2, while the waveform SET SHIFT DATA IN represents the output from AND gate 128.

The waveform SHIFT DATA IN represents the output from RS flip-flop 162. Finally, the waveform SHIFT CLOCK in FIG. 5 represents the output from NOR gate 164.

Referring to FIGS. 1 and 5, the RF SIGNAL from antenna 23 is converted to the RF DETECT signal by RF detect circuit 112. Note from FIG. 5 that the output from wake-up burst detect circuit 130 on line 156 is initially at a high logic level. In FIG. 5, a wake-up burst appears on the RF DETECT line 124 beginning at time T0 and ending at time T1. As previously noted, when a wake-up burst is detected in the output pulse stream from RF detect circuit 112 appears on line 124, wake-up burst detect circuit 130 deasserts its output. Thus, at time T1 in FIG. 5 when the RF DETECT signal makes a transition from a high to a low logic level, the CLOCK ENABLE output from NOR gate 132 makes a low-to-high transition, thereby enabling clock 136.

As would be apparent to those of ordinary skill in the art, the arrangement of clock 136 and counter 134 is such that counter 134 functions to count 4 kHz clock cycles from clock 136. Counter 134 is initially reset by wake-up burst in the RF DETECT signal; therefore at time T1, counter 134 begins counting from zero, and continues counting until time T2, when the RF DETECT signal rises. Thus, counter 134 effectively counts during the interval from the falling edge of the RF DETECT signal at time T1 until the rising edge of the RF DETECT signal at time T2, and the count value of counter 34 reflects the duration of this interval. That is, the count value represents the number of 244 μSec intervals occurring while clock 134 was enabled.

During the interval between times T2 and T3 in FIG. 5, another RF pulse is received by antenna 23 and converted into a logic pulse in the RF DETECT waveform. The high logic level of the RF DETECT signal during the pulse between times T2 and T3 causes counter 134 to be reset, since the RF DETECT signal is applied to the RESET input of counter 134. At time T3, when the RF DETECT pulse ends, clock 36 is once again enabled, due to the operation of NOR gate 132 as before. Thus, during the time interval between times T3 and T6, clock 36 is enabled and clock cycles are counted by counter 134.

At time T6, another RF burst is received by antenna 23, causing another data pulse in the RF DETECT waveform. Counter 34 is again reset, and at time T7 when the data pulse ends, clock 136 is enabled and counter 134 counts clock cycles.

The data pulse between times T6 and T7 resets counter 134, and at time T7, clock 36 is enabled.

As previously noted, the downlink telemetry encoding scheme for the presently disclosed embodiment of the invention is a variety of pulse interval modulation, in which the time between trailing edges of data pulses is used to indicate either "0" or "1" data. The start of data transmission is indicated by a "wake-up" pulse, which in the timing diagram of FIG. 5 is the long pulse designated generally as 172 in the RF SIGNAL waveform, during the interval between times T0 and T1. In FIG. 5, the time interval between the trailing edge of the RF SIGNAL at time T1 and the trailing edge of the RF SIGNAL at time T3 indicates a "0" data bit; the time interval between the trailing edges of the RF SIGNAL at times T3 and T7 indicate a "1" data bit. Since the data pulses, such as the one occurring in the RF SIGNAL between times T2 and T3, must be of a specified duration, the trailing-edge to trailing-edge encoding can also be interpreted by measuring the duration between the trailing edge of one pulse and the rising edge of the next pulse (e.g., the time interval between the trailing edge of the wake-up burst at time T1 and the rising edge of the data pulse at time T2).

As described above, counter 134 is operated to count during the time interval between the trailing edge of one pulse and the rising edge of the next pulse. Thus, the trailing-edge to rising-edge time interval. That is, for a longer trailing-edge to rising-edge time interval, the counter value of counter 134 will be greater than for a shorter trailing-edge to rising-edge time interval. Thus, a correspondence can be established between counter values and intervals in the RF SIGNAL stream.

In accordance with the present invention, PLA 150 is programmed to interpret different counter values as indicating different conditions. In particular, PLA 50 is programmed such that when counter 134 is allowed, by virtue of its being enabled and disabled as just described, to reach certain values, PLA 150 interprets the counter values as indicating received data bits. The correspondence between counter values and interpretation by PLA 150 is set forth in the following Table 1:

TABLE 1

| COUNTER VALUES | REAL-TIME VALUE | INTERPRETATION |
|---|---|---|
| 3–4 | 732–976 μSec | "0" bit |
| 9–10 | 2196–2440 μSec | "1" bit |

As set forth in Table 1, when counter 134 presents a value of three to the inputs of PLA 150, PLA 150 asserts its "0" output on line 158; likewise, when counter 134 presents a value of nine to the inputs of PLA 150, PLA 150 asserts its "1" output on line 160.

With continued reference to FIGS. 2 and 5, the "0" output from PLA 150 on line 158 is combined with the RF DETECT signal by AND gate 126. As would be appreciated by those of ordinary skill in the digital circuit art, then, if the "0" output from PLA 150 is asserted when the RF DETECT signal is asserted, the output from AND gate 126 will be asserted as well. On the other hand, if the RF DETECT signal is not asserted when the "0" output from PLA 150 is asserted, the output from AND gate 126 will remain at a low logic level.

Similarly, the "1" output from PLA 150 is ANDed with the RF DETECT signal by AND gate 128, so that if the RF DETECT signal is asserted when the "1" output on line 160 from PLA 150 is asserted, the output from AND gate 128 will also be asserted.

Asserting the output of AND gate 126 causes RS flip-flop 162 to be reset to a low logic output level. Asserting the output of AND gate 128 causes RS flip-flop 162 to be set to a high logic output level.

In the timing diagram of FIG. 5, the interval between times T1 and T2 has a trailing-edge to rising-edge duration corresponding to a "0" in the received RF pulse stream. Thus, at time T2, counter 134 will have counted three cycles of the 4 kHz clock signal on line 158 and will therefore be presenting a counter value of three (i.e., binary 1100, LSB to MSB) to the inputs of PLA 150; this is reflected in the waveforms COUNTER BIT 0 (LSB), COUNTER BIT 1, COUNTER BIT 2, and COUNTER BIT 3 (MSB) at time T2 in FIG. 5; in particular, at time T2, counter 134 has reached a count value of three (binary 1100). PLA 150 is programmed such that a value of three applied to its inputs results in assertion of the "0" output on line 158. As the "0" output on line 158 is asserted at time T2, the RF DETECT output from RF detect circuit 112 will rise to a high level, since the RF signal received by antenna 23 undergoes another RF burst beginning just after time T2. Thus, immediately after time T2, the RF detect signal on line 124 and the "0" output on line 158 will be simultaneously asserted, thereby asserting the output of AND gate 126 to reset flip-flop 162.

Assertion of the output from AND gate 126 also causes the normally asserted SHIFT DATA IN output of NOR gate 164 to be deasserted. This falling edge of the output from NOR gate 164 causes the logic level appearing at the output of flip-flop 162 to be shifted into shift register 166.

Thus, the following chain of events occurs beginning at time T0: Between times T0 and T1, a wake-up burst occurs, which is detected by wake-up burst detector 130. When the RF DETECT signal goes to a low logic level at time T1, clock 136 is enabled so that between times T1 and T2, counter 134 is allowed to count up to a value of three. This causes PLA 150 to assert its "0" PLA output on line 158 at time T2. At time T2, the RF DETECT signal on line 124 rises and is ANDed with the "0" output on line 158. The ANDing of the RF DETECT signal and the "0" output on line 124 results in assertion of the output from AND gate 126, which resets flip-flop 162 and causes the output of flip-flop 162 to be shifted into shift register 166. Since the assertion of the output from AND gate 126 resets flip-flop 162, a low logic level (i.e., a zero) is shifted into shift register 166.

The assertion of the RF DETECT signal on line 124 at time T2 causes counter 134 to be reset to a zero value in preparation for counting during the next trailing-edge to rising-edge interval in the RF DETECT signal.

In FIG. 5, the time interval between time T3 and T5 represents the trailing-edge to rising-edge interval for a "1" being transmitted. As before, clock 136 is enabled beginning at time T3, due to the low logic level signal of the RF DETECT signal being applied to NOR gate 132. Counter 134 counts clock cycles on line 138 throughout the entire interval between times T3 and T5. At time T4, counter 134 reaches a count value of three, which could represent a "0" in the pulse stream, as just described. The count value of three being applied to the inputs of PLA 150 causes PLA 150 to assert its "0" output on line 158 at time T3 as before. However, at time T3 the RF DETECT signal on line 124 has not risen to a high logic level as was the case at time T2. Therefore, assertion of the "0" output on line 158 does not cause the RESET SHIFT DATA IN output from AND gate 126 to be asserted, and furthermore does not cause the SHIFT DATA IN output from NOR gate 164 to be asserted.

At time T5, on the other hand, counter 134 reaches a value of nine, as shown, this value corresponding to a received "1" as described with reference to Table 1 above. The count value of nine being applied to the inputs of PLA 150 at time T5 causes PLA 150 to assert its "1" output on line 160. Also, just after time T5, the RF DETECT signal on line 124 rises to a high level, as shown in FIG. 5. The RF DETECT signal on line 124 and the "1" output from PLA 150 on line 160 are ANDed at AND gate 128. The assertion of the output signal from AND gate 128 (the SET SHIFT DATA IN signal) causes flip-flop 162 to be set. Also, assertion of the SET SHIFT DATA IN signal from AND gate 128 causes the SHIFT DATA IN output from NOR gate 164 to be deasserted, causing the output logic level from flip-flop 162 to be shifted into shift register 166. Since flip-flop 162 was set by AND gate 128, in this case a "1" is shifted into shift register 166 just after time T5.

The RF DETECT signal on line 124 rising after time T5, resets counter 134 and disables clock 136. At time T6, the RF DETECT signal on line 124 falls, beginning another interval corresponding to a "0" in the transmitted RF burst stream. As before, clock 136 is enabled at time T6 and counter 134 begins counting clock cycles. At time T7, counter 134 will have again reached a count value of three, causing the "0" output on line 158 from PLA 150 to be asserted. The "0" output is ANDed with the RF DETECT signal (asserted just after time T7) at AND gate 126, resetting flip-flop 162 and initiating a shift clock pulse to shift register 166. Thus, another "0" is shifted in to shift register 166.

Beginning at time T8, no further RF bursts appear in the RF SIGNAL. Counter 134, which is reset after time T7 and enabled at time T8 when the RF DETECT signal falls, begins counting clock cycles at time T8. At time T9, counter 134 reaches a count value of three and PLA 150 therefore asserts its "0" output signal. However, since the RF DETECT signal does not rise at time T9, no SHIFT DATA IN pulse is generated, and no data is shifted into shift register 166. Similarly, at time T10, counter 134 reachs a count values of nine and PLA therefore asserts its "1" output on line 160. Again, however, since the RF DETECT signal does not rise at time T10, no SHIFT DATA IN pulse is generated and no data is shifted into shift register 166.

Counter 134 reaches a count value of ten at time T11 in FIG. 5. PLA 150 is programmed such that it asserts the DISABLE DOWNLINK signal on line 154 whenever a value of ten is applied to its inputs. Thus, whenever the RF DETECT signal remains at a low logic level for ten clock cycles (i.e., 2440 μSec), the DISABLE DOWNLINK signal on line 154 is asserted. Assertion of the DISABLE DOWNLINK signal causes wake-up burst detect circuit 130 to assert its output on line 156, thereby preventing clock 136 from being enabled. Thereafter, counter 134 will have no clock cycles to count, and no outputs from PLA 150 will be asserted. Downlink telemetry is thus disabled, until another wake-up burst is detected.

Figure 6:
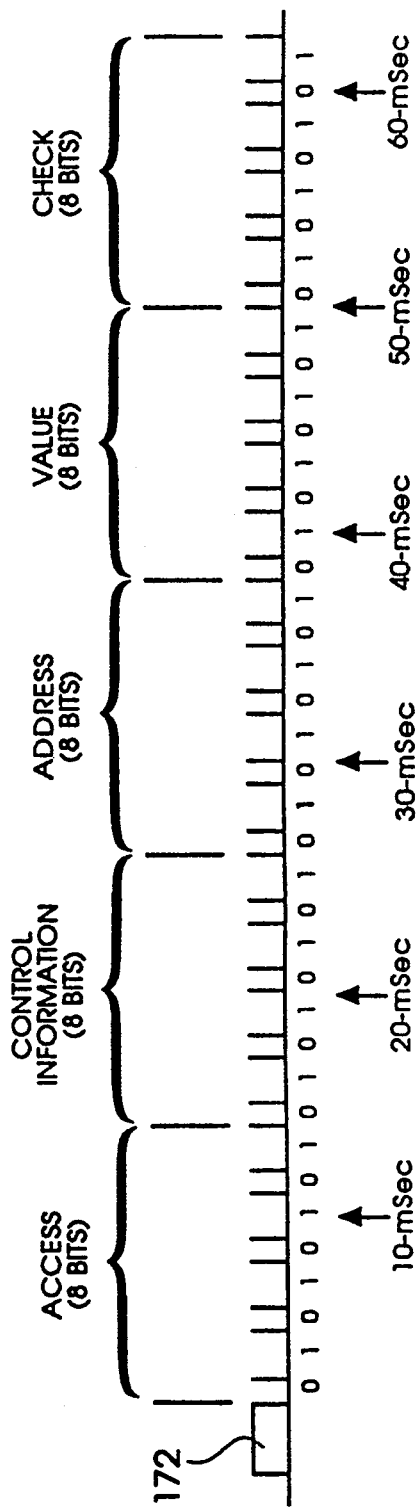
FIG. 6 is a diagram illustrating a downlink telemetry format supported by the telemetry system of FIG. 2.

In the embodiment of the invention depicted in FIG. 2, downlink telemetry data is demodulated as just described. A downlink telemetry format for the pulse-interval modulation protocol described with reference to FIG. 3 is shown in FIG. 6. In particular, a downlink message to device 10 begins with a wake-up burst, designated as 172 in FIG. 6, followed by five eight-bit bytes, each having a predetermined meaning. A first byte following wake-up burst 172, comprises an eight-bit access code for preventing inadvertent activation of telemetry system 33. A second byte following wakeup burst 172 contains eight bits of control information. A third byte contains address information identifying the type of information being transmitted, while a fourth byte contains the information value. Finally, eight bits at the end of the downlink message are used as check bits (e.g., parity bits) for detection/correction of errors in the downlink message.

As would be appreciated by those of ordinary skill in the art, the precise length of a downlink message having the format shown in FIG. 6 will vary depending upon the proportion of zeros and ones transmitted, since the modulating interval for a one is longer than that for a zero. Assuming an average of one-half zeros and one-half ones in the downlink message shown in FIG. 6, the entire message takes approximately 60 mSec to transmit.

Telemetry subsystem 33 of FIG. 2 is also employed in uplink telemetry, i.e., information transmitted from implanted device 10 to an external receiving device. In accordance with common practice in the industry, the modulation scheme employed for uplink telemetry is not the same as the pulse-interval modulation scheme described above for downlink telemetry. In the presently disclosed embodiment of the invention, uplink telemetry data is modulated using a pulse-position modulation technique, wherein a message frame is divided into a plurality of time slots, and wherein data is represented by either the presence or absence of an RF burst in each time slot.

Figure 7:
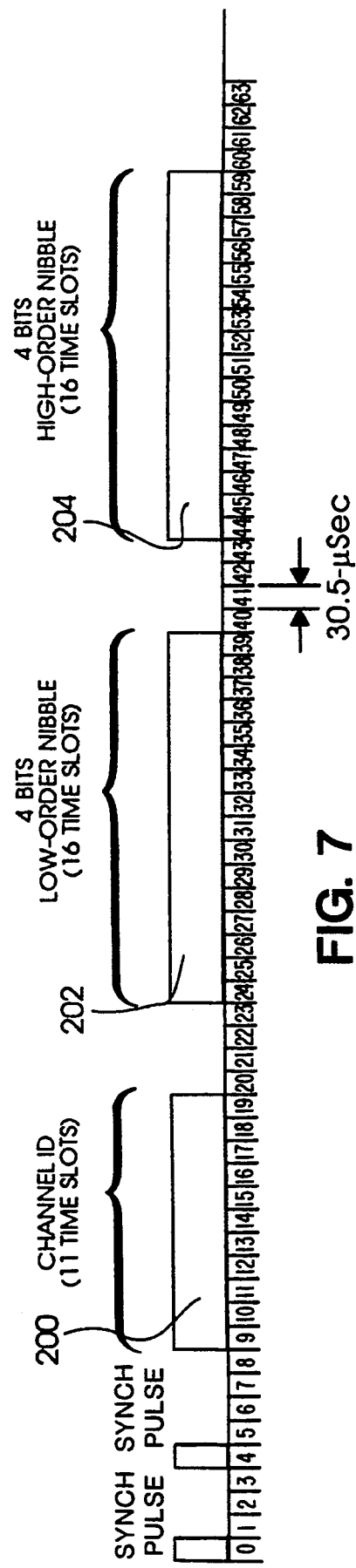
FIG. 7 is a diagram illustrating an uplink telemetry data frame supported by the telemetry system of FIG. 2.

Referring to FIG. 7, there is shown a data frame for the uplink telemetry protocol in accordance with the presently disclosed embodiment of the invention. The data frame of FIG. 7 consists of 64 separate time slots, each having a duration of 30.5 μSec. During uplink telemetry, an RF burst may or may not occur in each time slot in the frame of FIG. 7. An RF burst during a time slot represents a "1", while the absence of an RF burst during a time slot represents a "0". Each frame begins with an RF burst in time slots 0 and 4, with no RF bursts in time slots 1, 2, 3, 5, 6, 7, or 8. The RF bursts in time slots 0 and 4 are used for synchronization of the uplink telemetry transmitter and receiver.

In the eleven time slots 9 through 19, designated collectively as 200 in FIG. 7, data representing a telemetry channel identifier is transmitted. In the presently disclosed embodiment of the invention, telemetry circuit 33 may be employed to provide a number of separate telemetry channels between implanted device 10 and an external receiver. In particular, there are five different telemetry channels supported by telemetry circuit 33: an Idle channel, used for maintaining a telemetry link without communicating data between the implanted device and the external unit; a Waveform channel, for communicating digitized analog data; a Message channel, for communicating messages; a Marker channel, for communicating, in real time, "event markers" representing the occurrence of different cardiac events (see the above-reference Markowitz '382 patent); and a Handshake channel, for establishing a telemetry link between an implanted device and an external programming unit.

Time slots 24 through 39 in the uplink telemetry frame of FIG. 7, designated collectively as 202 therein, are used to encode the low-order nibble (four bits) of a byte of data transmitted by telemetry system 33. As would be appreciated by those of ordinary skill in the art, there are sixteen possible nibbles—i.e., sixteen different combinations of four binary digits: 0000, 0001, 0.010 . . . 1111. In accordance with the presently disclosed embodiment of the invention, each of the sixteen positions in the low order nibble section of the uplink telemetry data frame corresponds to one possible nibble. Thus, for example, an RF pulse in time slot 24 of the uplink telemetry data frame of FIG. 7 (i.e., the first time-slot in low-order nibble section 202) may be defined to correspond to the nibble 0000, position, time slot 25 may be defined to correspond to the nibble 0001, and so on, time slot 39 (the last time slot in low-order nibble section 202) corresponding to the nibble 1111.

With such an encoding scheme, an RF burst will occur in one and only one time slot in the low-order nibble section of the frame of FIG. 7.

Time slots 44 through 59 in the uplink telemetry frame of FIG. 7, designated collectively as 204, are used to encode the high-order nibble of a byte of uplink telemetry data. As with low-order nibble section 202 of the frame of FIG. 7, each of the sixteen time slots in high-order nibble section 204 are used to identify one of the sixteen possible high-order nibbles. Thus, an RF burst will occur in one and only one of the time slots in high-order nibble section 204 of the frame of FIG. 7.

It is contemplated that the uplink telemetry frame of FIG. 7 may further include additional time slots (not shown in FIG. 7) for encoding a "parity nibble", defined to be the bit-wise exclusive-OR of the low-order and high-order data nibbles. For example, additional time slots 64 through 79 could be defined to encode the parity nibble. A parity nibble as just described is believed to not be essential to the practicing of the present invention, but would enhance the telemetry system's noise immunity.

Figure 8:
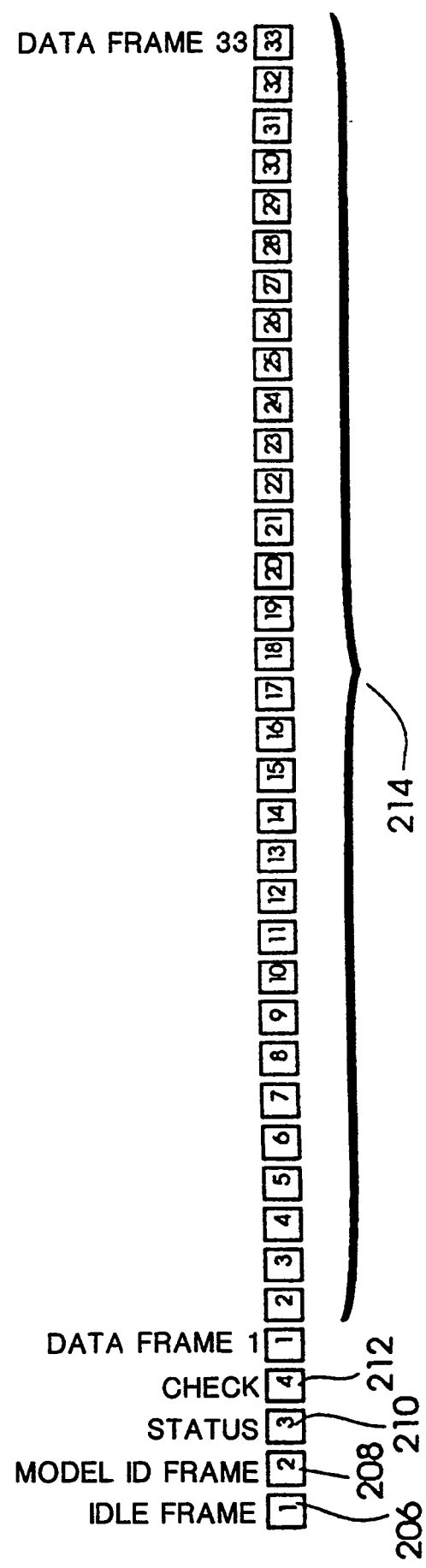
FIG. 8 is a diagram illustrating an uplink telemetry data record supported by the telemetry system of FIG. 2.

Further in accordance with the present invention, the uplink telemetry protocol defines an uplink telemetry record as comprising 37 frames of data, where each frame has the format previously described with reference to FIG. 7. A diagram of a telemetry record in accordance with the presently disclosed embodiment of the invention is provided in FIG. 8. The 37 frames of data in the uplink telemetry record of FIG. 8 are defined as follows: Frame 1, designated as 206 in FIG. 8, is an idle frame. Frame 2, designated as 208 in FIG. 8, is a frame used for identifying the model number of pacemaker 10. Frame 3, designated as 210 in FIG. 8, is a frame communicating status information in the uplink telemetry signal. Frame 4, designated as 212 in FIG. 8, contains error checking information for the record.

Frames 5 through 37, designated collectively as 214, in the uplink telemetry record of FIG. 8 are used to transmit data. Thus, each uplink telemetry record transmitted from device 10 contains four status/control frames, and thirty-three dam frames, each containing one byte of data. An entire uplink telemetry record, consisting of 37 frames of data, takes just over 70 mSec to transmit.

The uplink telemetry protocol described herein with reference to FIGS. 7 and 8 is substantially similar to that disclosed in the above-reference Wyborny et al. patent.

In accordance with the presently disclosed embodiment of the invention, uplink telemetry is accomplished using the same PLA 150 used for downlink telemetry.

As described above with reference to downlink telemetry in accordance with the presently disclosed embodiment of the invention, PLA 150 was conventional in design and operation. However, for the purposes of uplink telemetry, PLA 150 includes a RAM-programmable section 220 that is not used for downlink telemetry. Section 220 of PLA 150 is coupled to receive nibbles of data in parallel form via an eight-bit bus 222 that is also coupled to the respective bit positions of shift register 166. Bus 222 couples telemetry system 33 to digital controller 31, as shown in FIG. 2, or may couple telemetry system 33 directly to data and control bus 30 in device 10, so that bus 222 could be used to couple telemetry system 33 directly to microcomputer circuit 24. Whether telemetry system 33 is coupled directly to microcomputer circuit 24 or indirectly, through digital circuit 31, is considered to be a design option which may be exercised in various ways depending upon the particular implementation. For the purposes of the following description, it is sufficient to describe bus 222 as coupling telemetry circuit 33 to some source of uplink telemetry data, whether it be microcomputer circuit 24 or digital controller circuit 31.

As shown in FIG. 2, four bit lines of bus 222 control one output term 224 of PLA 150, while the remaining four bit lines of bus 222 control another output term 226 of PLA 150. Programmable section 220 of PLA 150 is controlled by means of a PROGRAM input signal to PLA 150, the PROGRAM input signal being supplied from digital controller circuit 31 (or from microcomputer circuit 34, depending upon the implementation). Programmable section 220 of PLA 150 functions to latch the eight data bits on bus 222 into the eight locations in programmable section 220 corresponding to the output terms 224 and 226 upon assertion of the PROGRAM input signal. In this way, the decode value for terms 224 and 226 can be dynamically reprogrammed during uplink telemetry operation. Once programmed, output terms 224 and 226 behave as conventional output terms, asserting their respective outputs whenever input signal s from counter 134 and flip-flop array 148 match the programmed values in programmable section 220. In particular, the output lines from programmable PLA terms 224 and 226 are coupled to the TELEMETRY OUT output from PLA 150.

Figure 9:
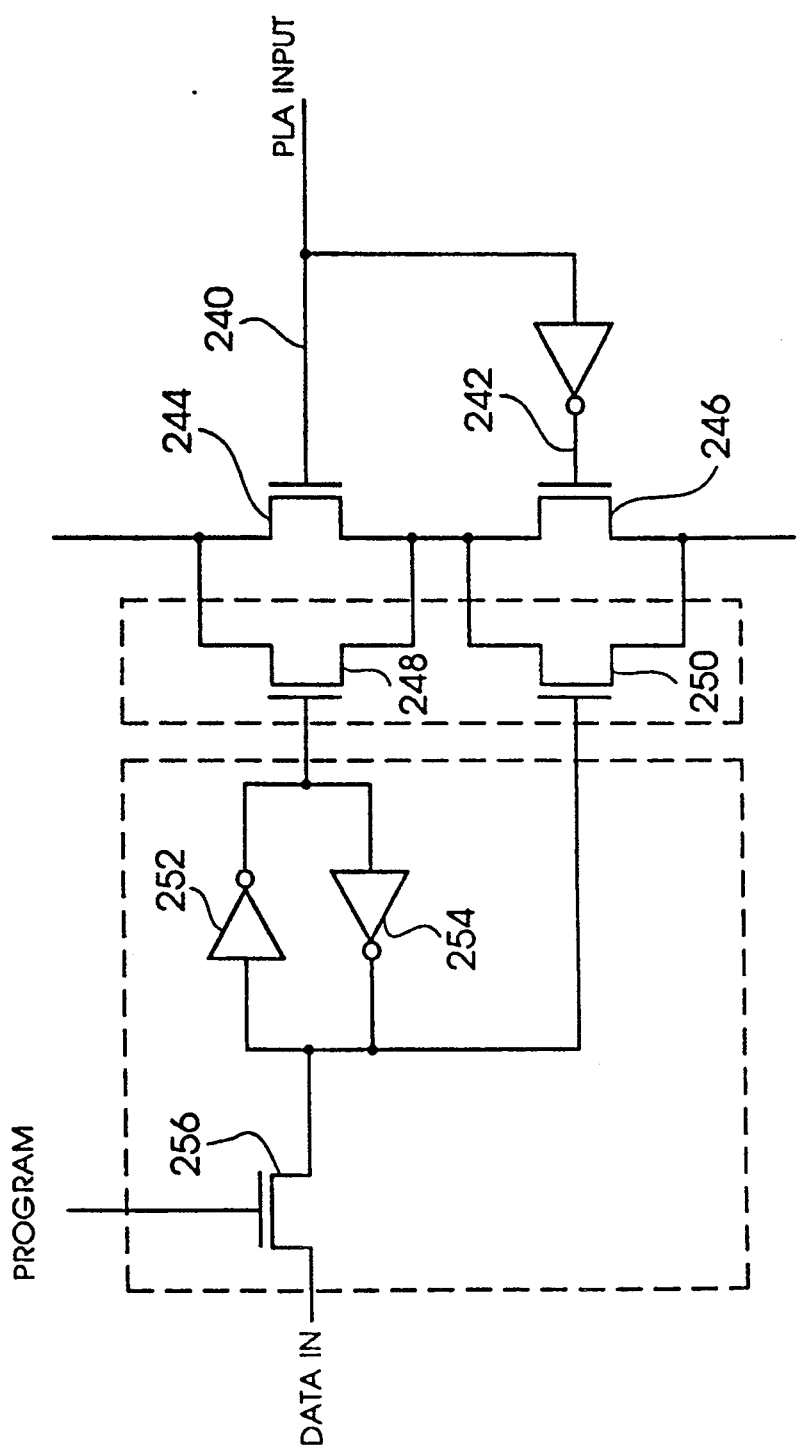
FIG. 9 is a schematic diagram of a programmable section of the programmed logic array in the telemetry circuit of FIG. 2.

In FIG. 9, there is shown one possible implementation of programmable section 220 of PLA 150. The circuit of FIG. 9 represents a single programmable bit in programmable section 220. As in conventional PLA cells, the programmable PLA cell of FIG. 9 receives an input signal and its inverse on lines designated 240 and 242. These signals are applied to the gates of transistors 244 and 246, respectively. Coupled with transistor 244 is a second transistor 248, and coupled with transistor 246 is a second transistor 250. The gates of transistors 248 and 250 are coupled to a latch comprising inverters 252 and 254; in particular, the gate of transistor 250 is coupled to the output of inverter 254, while the gate of transistor 248 is coupled to the output of inverter 252.

The state of the latch formed by inverters 252 and 254 is programmable by means of the PROGRAM input signal, which is applied to the gate of a transistor designated as 256 in FIG. 9. When the PROGRAM signal is asserted, transistor 256 is rendered conductive, thereby setting the state of the latch formed by inverters 252 and 254 according to the signal then being applied to the DATA input in FIG. 9. After the PROGRAM signal is deasserted, the DATA value is latched in the cell.

Although a particular implementation of a programmable section of PLA 150 has been described herein in some detail, it is believed that an equivalent circuit could be implemented in any of various ways by persons skilled in the art.

Each of the programmable output terms 224 and 226 in FIG. 2 corresponds to four of the programmable PLA cells depicted in FIG. 9. In accordance with the presently disclosed embodiment of the invention, each byte of uplink telemetry data to be transmitted from device 10 to an external receiver is first programmed into the eight programmable locations in programmable section 220 of PLA 150.

For uplink telemetry, clock 136 generates a 32 kHz clock signal on line 138, whereas for downlink telemetry, clock 136 was described as a 4 kHz clock. In one implementation of the present invention, a single 32 kHz clock 136 is used, and a clock divider circuit, not shown in the figures, is used to derive the 4 kHz clock signal needed for downlink telemetry. It is also contemplated that separate uplink and downlink telemetry clocks could be provided. Alternatively, a single 32 kHz clock could be employed, provided that PLA 150 was reprogrammed with different downlink telemetry terms, since the number of clock cycles in each trailing-edge to trailing-edge interval would be eight times as great for a 32 kHz clock as for a 4 kHz clock. The selection of one of these design options is not believed to be critical to understanding or practicing the present invention.

Once a byte of uplink telemetry data has been programmed into the eight programmable PLA cells of output terms 224 and 226, clock 136 is enabled by assertion of the UPLINK ENABLE signal applied to the ENABLE input of clock 136. The UPLINK ENABLE signal is provided from digital controller/timer circuit 31 (or directly from microcomputer circuit 24, as previously described).

The 32 kHz clock signal on line 138 causes counter 134 to be incremented once for each clock cycle. Each time the output from clock 134 matches an output term in PLA 150, the output signal corresponding to that term is asserted, as in a conventional PLA.

As shown in FIG. 2, a number of PLA outputs are fed back into three-bit flip-flop array 148, on lines designated 262, 264, and 266. Similarly, one PLA output is fed back on line 260 to a RESET input to counter 134. Flip-flop array 148 functions as a state register, and the contents of the state register 148 are applied as input terms to PLA 150. Another output line from PLA 150, designated as TELEMETRY OUT in FIG. 2, is coupled to a telemetry driver circuit (not shown). When a pulse is produced on the TELEMETRY OUT output line, this pulse causes the telemetry driver circuit to "ring" the telemetry coil, thereby producing an RF burst that is transmitted to the external receiver. As noted above, the PLA outputs corresponding to programmable terms 224 and 226 are coupled to the TELEMETRY OUT output line, so that when a match between input terms from counter 134 and state register 148 and one of the programmable terms 224 or 226 occurs, a telemetry pulse (RF burst) is transmitted.

Another output from PLA 150 is designated with reference numeral 260 in FIG. 2 and is coupled to the RESET input to counter 134. Thus, a correspondence between some term in PLA 150 and the inputs thereto will result in counter 134 being reset, as will be hereinafter described in greater detail.

Three other outputs from PLA 150, designated with reference numerals 262, 264, and 266 in FIG. 2, are applied to the inputs of three flip-flop state register 148. As previously noted, the outputs from state register 148 are applied as inputs to PLA 150. This feed-back arrangement of output lines 262, 264 and 266 is such that the state variable stored in state register 148 can be set according to correspondence between certain input combinations to PLA 150.

Still another output from PLA 150, designated by reference numeral 268 in FIG. 2, indicates when a frame of data has been transmitted. This signal may be provided, for example, to microcomputer circuit 24 or microcontroller circuit 22 to provide an indication that telemetry circuit 33 is ready for further uplink telemetry operation.

In the following Table 2, there is set forth the correspondence between certain input terms and the behavior of PLA 150 in response thereto:

TABLE 2

| TERM NUMBER | INPUTS | | | | | | | OUTPUTS ASSERTED | S2' | S1' | S0' |
|---|---|---|---|---|---|---|---|---|---|---|---|
| | C3 | C2 | C1 | C0 | S2 | S1 | S0 | | | | |
| 1 | 0 | 0 | 0 | 0 | 0 | 0 | 0 | TELEMETRY OUT | 0 | 0 | 0 |
| 2 | 0 | 1 | 0 | 0 | 0 | 0 | 0 | TELEMETRY OUT | 0 | 0 | 0 |
| 3 | 1 | 0 | 0 | 0 | 0 | 0 | 0 | RESET COUNTER | 0 | 0 | 1 |
| 4 | (CHANNEL ID) | | | | 0 | 0 | 1 | TELEMETRY OUT | 0 | 0 | 1 |
| 5 | 1 | 0 | 1 | 1 | 0 | 0 | 1 | RESET COUNTER | 0 | 1 | 0 |
| 6 | 0 | 1 | 0 | 0 | 0 | 1 | 0 | RESET COUNTER | 0 | 1 | 1 |
| 7 | (TERM 224) | | | | 0 | 1 | 1 | TELEMETRY OUT | 0 | 1 | 1 |
| 8 | 0 | 0 | 0 | 0 | 0 | 1 | 1 | RESET COUNTER | 1 | 0 | 0 |
| 9 | 0 | 1 | 0 | 0 | 1 | 0 | 0 | RESET COUNTER | 1 | 0 | 1 |
| 10 | (TERM 226) | | | | 1 | 0 | 1 | TELEMETRY OUT | 1 | 0 | 1 |
| 11 | 0 | 0 | 0 | 0 | 1 | 0 | 1 | RESET COUNTER | 1 | 1 | 0 |
| 12 | 0 | 1 | 0 | 0 | 1 | 1 | 0 | END OF FRAME | 0 | 0 | 0 |

In Table 2 above, the left half ("INPUTS") specifies a combination of inputs, while the right half ("OUTPUTS") identifies what output lines are asserted in response to the specified inputs. For example, term number 1 in Table 2 indicates that when a counter value of zero (i.e., {C3 C2 C1 C0}={0000}) and a state variable of zero (i.e., {S2 S1 S0}={000}) are applied to the inputs of PLA 150, TELEMETRY OUT is asserted, and the output signals on lines 262, 264, and 266 (the "new state" variable) are at a low logic level. Thus, in response to the inputs listed in term number 1 in Table 2, an RF burst is transmitted and the state machine remains in state zero (i.e., {S2'S1' S0'}={000}).

Term number 2 in Table 2 indicates that when a counter value of four (i.e., {C3 C2 C1 C0}={0 10 0})

and a state variable of zero are applied to the inputs of PLA 150, TELEMETRY OUT is asserted and the state machine remains in state zero (i.e., the signals on lines 262, 264, and 266 are held at a low logic level).

Term number 3 in Table 2 indicates that when a counter value of eight (i.e., {C3 C2 C1 C0}={0000}) and a state variable of zero are applied to the input of PLA 150, the RESET COUNTER output on line 260 from PLA 150 is asserted. Also, the "new state" state variable is set to a value of one (i.e., the signals on lines 262, 264, and 266 are at high, low, and low logic levels, respectively). Thus, in response to the input signal combination listed for term number 3 in Table 2, the state machine implemented by PLA 150 goes from state zero to state one, and counter 134 is reset.

Term number 4 in Table 2 lists "Channel ID" as the counter value input term, and state one as the state register input term. In the presently disclosed embodiment of the invention, PLA 150 is programmed with one term for the channel ID value. Term 4 in Table 2 indicates that when the current state value is one (i.e., {S2 S1 S0}={001}) and a match between the value from counter 134 and the channel ID occurs, a telemetry, pulse is generated by assertion of the TELEMETRY OUT signal.

Term number 5 in Table 2 indicates that when the current state value is one and the value from counter 134 is eleven (i.e., {C3 C2 C1 C0}={10 11}), counter 134 is reset by assertion of the signal on output line 260, and a new state value of two (i.e., {S2 S1 S0}={010}) is loaded into state register 148.

Term number 6 in Table 2 indicates that when the current state value is two and the value from counter 134 is four, counter 134 is reset and a new state value of three is loaded into register 148.

Term number 7 in Table 2 indicates that when the current state value is three and the value from counter 134 reaches the value programmed into programmable term 224 in PLA 150, a telemetry pulse is generated; the state value remains at three.

Term number 8 in Table 2 indicates that when the current state value is three and the value from counter 134 reaches zero (i.e., when the counter increments from fifteen (1111) to sixteen (0000)), counter 134 is reset and a new state value of four is loaded into state register 148.

Term number 9 in Table 2 indicates that when the current state value is four and counter 134 reaches a value of four, counter 134 is reset and a new state value of five is loaded into state register 148.

Term number 10 in Table 2 indicates that when the current state value is five and counter 134 reaches a value which matches the bits programmed into programmable term 226 in PLA 150, a telemetry pulse is generated.

Term number 11 in Table 2 indicates that when the current state value is five and counter 134 reaches zero (i.e., when counter 134 has counted to sixteen, as with term 8 above), counter 134 is reset and a new state value of six is loaded into state register 148.

Finally, term number 12 in Table 2 indicates that when the current state value is six and counter 134 reaches a value of four, the END OF FRAME output signal on line 268 is asserted.

Uplink telemetry proceeds as follows: First, two nibbles of data, to be transmitted in fields 202 and 204 of an uplink telemetry frame (see FIG. 7) are programmed into programmable terms 224 and 226 of PLA 150. Then, the UPLINK ENABLE signal is asserted, thereby allowing the 32-kHz clock signal from clock 136 to be applied to the input of counter 134.

Counter 134 and state register 148 are initially set to zero; when clock 136 is enabled, counter 134 begins counting clock cycles. Before counter 134 increments from zero to one, however, the counter value will be zero and the state value in register 148 will be zero. As indicated in term 1 of Table 2 above, PLA 150 is programmed to respond to this condition (count=zero, state=0) by asserting the TELEMETRY OUT signal to initiate transmission of an RF telemetry pulse. This pulse corresponds to the synchronization pulse in time slot 0 of the uplink telemetry frame of FIG. 7.

Counter 134 will next count clock pulses until it reaches a counter value of four: the state value will still be zero. As indicated in term 2 of Table 2 above. PLA 150 is programmed to respond to this condition (count=4, state=0) by asserting the TELEMETRY OUT signal to initiate transmission of an RF telemetry pulse. This pulse corresponds to the synchronization pulse in time slot 4 of the uplink telemetry frame of FIG. 7.

Counter 134 will continue counting clock pulses until it reaches a count value of eight; the state value will still be zero. As indicated in term 3 of Table 2 above, PLA 150 is programmed to respond to the condition (count=8, state=0) to assert the signal on line 260, thereby resetting counter 134 to a zero count value. Also, a new state value of one (i.e., {S2 S1 S0}={001}) is loaded into state register 148. This occurs at time slot eight in the uplink telemetry frame of FIG. 7.

With the state register now indicating to PLA 150 that the current state is one, counter 134 will begin counting from zero. Thereafter, when the counter value reaches the value corresponding to the current telemetry channel ID value, term 4 of Table 2 indicates that PLA 150 will initiate a telemetry pulse by asserting the TELEMETRY OUT signal. This telemetry pulse occurs during the CHANNEL ID section 200 of the uplink telemetry frame of FIG. 7, and its position in section 200 identifies the channel that the current frame corresponds to.

After the channel ID pulse is delivered, counter 134 will continue counting until it reaches a value of eleven. As indicated by term 5 of Table 2 above, PLA 150 is programmed to respond to this condition (count=11, state=1) to reset counter 134 and load a new state value of two into state register 148. This occurs at time slot 19 in the uplink telemetry frame of FIG. 7.

Counter 134 thus begins counting from zero, beginning with time slot 20 of the uplink telemetry frame of FIG. 7. When counter 134 reaches a count value of four, term 6 of Table 2 indicates that PLA 150 will respond by asserting the signal on line 260 to reset counter 134, and enter a new state value of three into state register 148. This occurs at time slot 23 in the uplink telemetry frame of FIG. 7.

Counter 134 next begins counting from zero. As indicated by term 7 of Table 2, when the count value of counter 134 reaches a value corresponding to the data previously programmed into programmable term 224 of PLA 150, PLA responds by asserting the TELEMETRY OUT signal to initiate transmission of a telemetry pulse. This pulse will occur during one of the time slots (2–39) in the low-order nibble section 202 of the uplink telemetry frame of FIG. 7. The position of this pulse in section 202 of the frame corresponds to the programmed data value in term 224 of PLA 150. That is, assuming that the sixteen time slots in low-order nibble section 202 of the uplink telemetry frame are numbered from zero to fifteen, if a binary value of four is programmed into term 224 of PLA 150, a telemetry pulse will be transmitted in the fifth time slot (time slot 4) of section 202 of the frame. A binary value of zero programmed into term 224 will cause a telemetry pulse to be transmitted in the first time slot (time slot 0) of section 202.

After transmission of a pulse during one of the time slots in section 202 of the data frame, counter 134 will continue counting until it reaches a count value of zero (i.e., when it increments from fifteen); the state value will still be three at this point. As indicated by term 8 in Table 2, PLA 150 is responsive to this condition (count −0, state =3) to reset counter 134 and load a new state value of four into state register 148. This occurs at time slot 39 in the uplink telemetry data frame of FIG. 7 (i.e., the last time slot in low-order nibble section 202 of the data frame).

Now in state four, counter 134 will count until it reaches a value of four. As indicated by term 9 of Table 2, when counter 134 reaches a count value of four when in state four, PLA 150 responds by resetting counter 134 and loading a new state value of five into state register 148. This occurs in time slot 43 of the uplink telemetry data frame of FIG. 7.

In state five, counter 134 will begin counting from zero until its count value matches the value programmed into programmable term 226 in PLA 150. At this point, PLA 150 will assert the TELEMETRY OUT signal to initiate transmission of a telemetry pulse, as indicated by term 10 of Table 2. This pulse will be delivered during high-order nibble section 204 of the data frame of FIG. 7, and as with the pulse delivered during low-order nibble section 202, the pulse will be transmitted during the nth time slot of section 204 when a value of (n-1) is programmed into programmable PLA term 226.

After transmission of a telemetry pulse during one time slot of high-order nibble section 204 of the data frame, counter 134 will continue counting until it reaches a zero value (i.e., after it increments from a value of fifteen). Term 11 of Table 2 indicates that in response to this condition (count=0, state≦5), PLA 150 will assert the signal on line 260 to reset counter 134, and will load a new state value of six into state register 148. This occurs at time slot 59 in the uplink telemetry frame of FIG. 7, the last time slot in high-order nibble section 204.

With the state machine in state six, counter 134 will begin counting from zero until it reaches a value of four. According to term 12 of Table 2, PLA 150 will respond to this condition (count=4, state=6) by asserting the END OF FRAME signal on line 268. This occurs at the last time slot in the uplink telemetry frame of FIG. 7.

As would be appreciated by those of ordinary skill in the art, telemetry circuit 33 of FIG. 2 can be configured to operate with many different types of telemetry formats by stepping from state to state via feedback state register 148. All parameters of the telemetry protocol can be adjusted by specifying the frequency of clock 136, the width of counter 134, the bit with of programmable PLA terms 224 and 226 (and/or the inclusion of more than two programmable nibbles in PLA 150), and the number of allowable state values. For both uplink and downlink telemetry for the system of FIG. 2, more than one telemetry protocol can be programmed into a single PLA 150.

Figure 10:
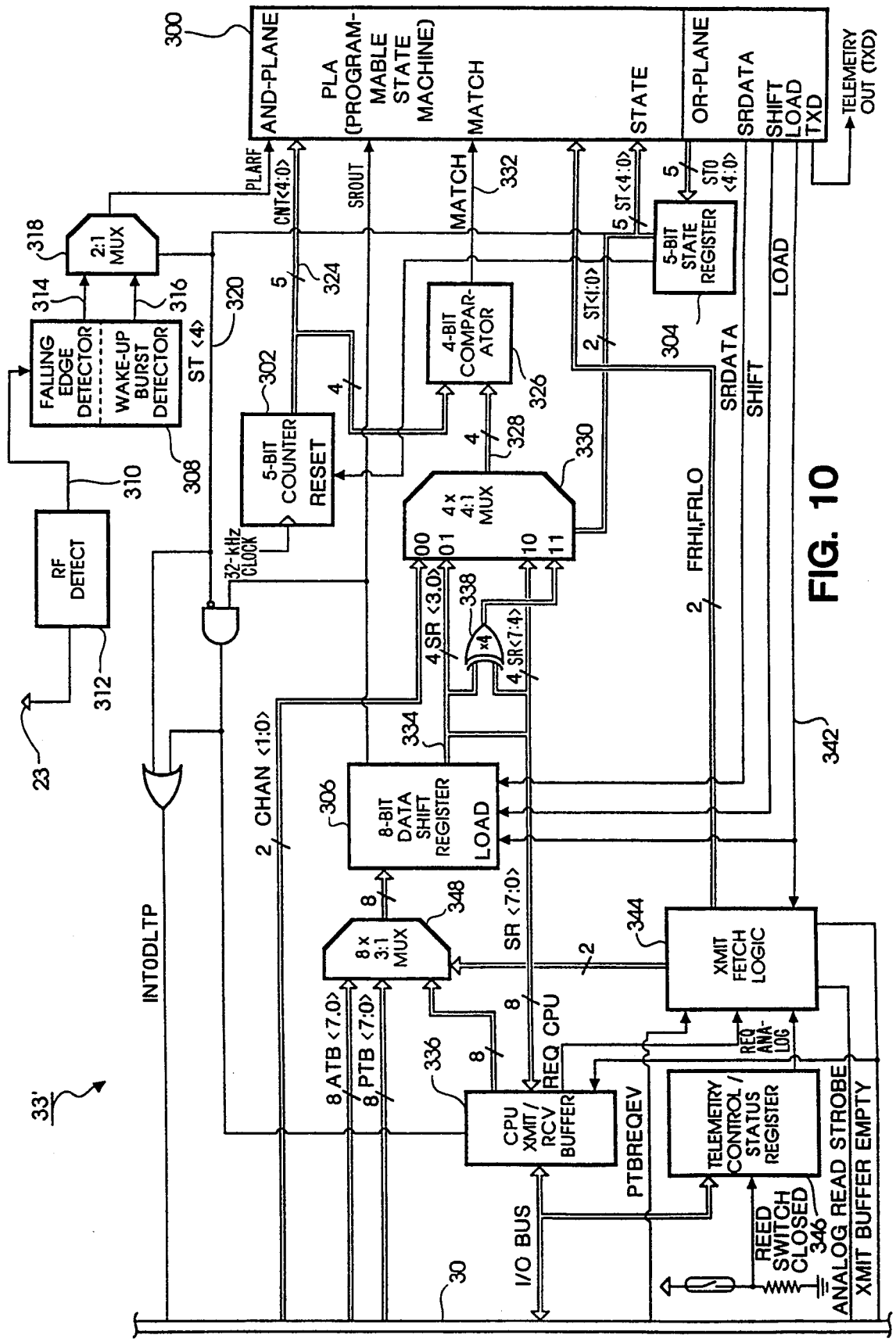
FIG. 10 is a block diagram of a telemetry system in accordance with another embodiment of the invention.

Turning now to FIG. 10, there is shown a block diagram of a telemetry subsystem 33′ in accordance with another embodiment of the present invention. As with telemetry system 33 of FIG. 2, telemetry system 33′ of FIG. 10 is a PLA-based circuit operable in conjunction with an implantable device such as the pacemaker 10 of FIG. 1.

Referring to FIG. 10, telemetry circuit 33′ includes a PLA 300, a five-bit counter 302, a five-bit state register 304, and an eight-bit shift register 306. For downlink telemetry, circuit 33′ includes a falling edge detector and wake-up burst detector 308, coupled to receive a RF DETECT signal on line 310 from an RF detect circuit 312. As with RF detect circuit 112 in the embodiment of the invention shown in FIG. 2, RF detect circuit 312 in circuit 33′ of FIG. 10 receives the received signal from antenna 23 and converts the stream of RF pulses to a stream of digital logic pulses. Falling edge detector and wake-up burst detector circuit 308 functions to assert an output signal on a first output line 314 upon detecting falling edge in the RF DETECT signal on line 310, and further to assert an output signal on a second output line 316 upon detection of a wake-up burst in the RF DETECT signal, as previously described with reference to FIG. 3.

The signals on lines 314 and 316 indicating falling edges and wake-up bursts, respectively, are applied to the inputs of a 2:1 multiplexer 318, the output of which is applied to a PLARF input to PLA 300. Thus, either the falling edge signal on line 314 or the wake-up burst signal on line 316 can be applied to the PLARF input of PLA 300, depending upon the logic level of a control signal applied on line 320 to the control input of multiplexer 318. The signal on line 320 is derived from one bit of five-bit state register 304; in particular, the signal on line 320 reflects the fifth state bit, ST<4>.

All five state register bits ST<4:0>are applied via bus 322 to a STATE input of PLA 300.

The five bits CNT<4:0>reflecting the count value of counter 302 are also applied as inputs to PLA 300, on bus 324. Bus 324 also conveys four of the count bits, CNT<3:0>to a four-bit input of a comparator 326. Another input of four-bit comparator 326 receives four signals on bus 328 from the output of a 4×4:1 multiplexer 330. The output of comparator 326 is conducted on line 332 to a MATCH input to PLA 150. The signal on line 332 is asserted when the four count value bits CNT<3:0>on bus 324 are found to match the four bits on line 328 supplied from multiplexer 330.

Eight bits of data from the eight positions SR<7:0>of shift register 306 are presented on eight-bit bus 334. Four of the shift register bits, SR<3:0>, are applied to a first four-bit input (00) of multiplexer 330. The remaining four bits SR<7:4>are applied to a second four-bit input (10) of multiplexer 330. All eight shift register bits SR<7:0>are applied to an input of a CPU transmit/receive buffer 336.

As shown in FIG. 10, the first four shift register bits SR<3:0>and the second tour shift register bits SR<7:4>are applied to separate inputs of a four-bit exclusive-or (4×XOR) circuit 338. 4×XOR circuit 338 performs a bit-wise logical exclusive-or function on the shift register bits; that is, bit SR<7>is exclusive-ORed with bit SR<3>, bit SR<6>with bit SR<2>, bit SR<5>with bit SR<1>, and bit SR<4>with bit SR<0>. The four exclusive-or results are then applied to a third four-bit input (11) of 4×4:1 multiplexer 330. 4×XOR circuit 338 is employed to provide the "parity nibble" for an uplink telemetry frame, as previously described with reference to FIG. 7.

As shown in FIG. 10, telemetry circuit 33' in accordance with the presently disclosed embodiment of the invention is preferably coupled directly to data and control bus 30 of microcomputer circuit 24, although as with the embodiment of FIG. 2, it is contemplated that circuit 33' may be coupled to microcomputer circuit indirectly, via digital controller/timer circuit 31.

As previously noted, pacemaker 10 from FIG. 1 preferably supports a plurality of different telemetry channels (e.g., Idle, Waveform, Message, Marker, and Handshake). A different uplink telemetry frame may be defined for each different channel. In order to identify to PLA 300 what channel an uplink message is to be transmitted on (and thus what type of uplink frame to transmit), two signals FRHI and FRLO are applied as inputs to PLA 300. In addition, to further identify to PLA 300 which of several possible waveforms is present on the waveform channel, two bits, CHAN<1:0>, are supplied from ADC and multiplexer 36 and applied via a two-bit bus 340 to a fourth input (00) of multiplexer 330. The CHAN<1:0>bits allow the telemetry system in accordance with the presently disclosed embodiment of the invention to encode different waveforms uniquely (i.e., with a unique "type pulse" position) via transition 448.

PLA 300 in telemetry circuit 33' of FIG. 10 has an output line TELEMETRY OUT (TXD) which, as in the embodiment of FIG. 2, is coupled to a telemetry driver circuit (not shown) capable of "ringing" telemetry coil 23 to transmit an RF pulse.

Another output signal LOAD from PLA 300 is conducted on line 342 to a LOAD input to shift register 306 and to a FETCH input of a transmit fetch logic circuit 344. Transmit fetch logic circuit 344 cooperates with CPU transmit/receive buffer 336, a telemetry control/status register 346, and an eight-bit 3:1 (8×3:1) multiplexer 348 to obtain uplink telemetry data from microcomputer circuit 24. In particular, when data is to be uplink telemetered from pacemaker 10, microcomputer circuit 24 provides the data, one byte at a time on data/control bus 30, to CPU transmit/receive buffer 336. From buffer 336, the data to be transmitted is provided to shift register 306 via 8×3:1 multiplexer 348. Obtaining uplink telemetry data in this way is initiated when PLA 300 asserts the FETCH output signal on line 342.

Downlink telemetry data received and demodulated by telemetry circuit 33' is shifted one bit at a time into shift register 306, as will be hereinafter described in greater detail, and then transferred in parallel from shift register 306 on bus 334 to CPU transmit/receive buffer 336, and from there to microcomputer circuit 24 on bus 30.

It is believed by the inventors that there are various acceptable ways to implement circuitry for interfacing telemetry circuit 33' with a source of uplink telemetry data (e.g., microcomputer circuit 24) and to a destination for downlink telemetry data. Thus, although a particular interface, including transmit fetch logic 344, telemetry control/status register 346, CPU transmit/receive buffer, and multiplexer 348, is depicted in FIG. 10, this circuitry will not be described herein in further detail. For the purposes of the present disclosure, it is sufficient to assume that uplink telemetry data is supplied to shift register 306 as needed, and that downlink telemetry data is provided on bus 334 as it is received.

For downlink telemetry, the embodiment of the invention shown in FIG. 10 supports a pulse-interval modulation telemetry protocol substantially similar to that described above with reference to the embodiment of FIG. 2 and the example RF SIGNAL waveform of FIG. 3. In particular, the downlink telemetry format prescribes a wake-up burst (like burst 50 in FIG. 3) having a duration of 2000 $\mu$Sec±50 $\mu$Sec. Data bursts (like data bursts 52, 54, and 56 in FIG. 3) are prescribed to have a width of 200 $\mu$Sec±50 $\mu$Sec. An interval of no data bursts of 6000 $\mu$Sec or more is interpreted as an end-of-transmission marker.

According to the downlink telemetry format supported by the embodiment of FIG. 10, a binary "0" bit is encoded as an interval of between 600 $\mu$Sec and 750 $\mu$Sec between successive data pulse trailing edges. Similarly, a binary "1" bit is encoded as an interval of between 1070 $\mu$Sec to 1220 $\mu$Sec between trailing edges.

Uplink telemetry for the embodiment of the invention shown in FIG. 10 uses a pulse-position modulation protocol identical to that described above with reference to FIGS. 7 and 8.

Telemetry circuit 33' in FIG. 10, like telemetry circuit 33 in FIG. 2, operates as a state machine, in which various input variables and a multi-bit state variable are applied to PLA 300, causing PLA 300 to assert various output signals and to specify the next state for the state machine to enter. As in the previously disclosed embodiment, the embodiment of FIG. 10 utilizes counter (in FIG. 10, counter 302), to measure the duration between trailing edges of the received downlink telemetry RF pulse stream. The counter value at the occurrence of each data pulse trailing edge thus reflects the duration of the interval between successive trailing edges, and PLA 300 takes appropriate actions depending upon that duration.

In the following Table 3, the interpretation of various counter values for counter 302 is provided:

TABLE 3

| COUNTER VALUES | REAL-TIME VALUE | INTERPRETATION |
|---|---|---|
| 2–15 | 30–489 $\mu$Sec | Error |
| 16–28 | 457–886 $\mu$Sec | "0" bit |
| 29–32 | 854–1008 $\mu$Sec | Error |
| 33–46 | 976–1435 $\mu$Sec | "1" bit |
| 47+ | >1403 $\mu$Sec | Error |

The timebase for both uplink and downlink in the embodiment of FIG. 10 is a 32 kHz clock (i.e., a clock having a 30.5 $\mu$Sec cycle). Notice from Table 3 that in the second embodiment of the invention, the "resolution" of interval measurement is greater as compared with the 4 kHz embodiment of FIG. 2, since each cycle of the 32 kHz clock is smaller with respect to the intervals being measured.

As set forth in Table 3, when counter 302 presents any of the values in the range between two and fifteen (inclusive) to the inputs of PLA 300, PLA 300 interprets this is being an error condition; that is, an interval of 30- to 489 $\mu$Sec between the trailing edges of two consecutive data pulses is not a valid or meaningful one according to the pulse interval modulation protocol employed by the presently disclosed embodiment of the invention.

On the other hand, if counter 302 presents any of the values between 16 to 28 (inclusive) to PLA 300, PLA 300 interprets this as an indication that a "0" bit has been detected in the RF pulse stream. This is because those count values correspond to a realtime interval of between 457- and 886 μSec; such an interval between trailing edges of consecutive data pulses corresponds the downlink encoding of a "0" bit.

Similarly, if counter 302 presents a value in the range between 33 and 46 (inclusive) to PLA 300, this is interpreted as indicating a detection of a "1" bit in the data stream, since the corresponding real-time interval to such a range of clock values (i.e., 976- to 1435 μSec) between trailing edges of consecutive data pulses is the pulse interval encoding of a "1" bit.

If counter 302 presents a value in the range between 29 and 32 (inclusive) to PLA 300, this is interpreted as an error. Likewise, if counter 302 is allowed to count to a value of 47 or greater, this is interpreted as an error. One or more detected errors in the received pulse stream indicates a poor or incompatible signal, and causes microprocessor circuit 24 to discard the message.

It is to be noted that the interpretation values set forth in Table 3 above reflect an approximately 30 μSec overlap between "adjacent" classifications. For example, Table 3 indicates that an interval in the range between 854- and 886-μSec can be classified as either an error or a "0" bit. This phenomenon inherently arises from the use of a clock having a 30.5 μSec cycle time to synchronize incoming data.

It is also to be noted that although a 5-bit counter 302 is used, the values in Table 3 indicate that counter values of 47 or more may be applied to PLA 300. As would be appreciated by those of ordinary skill in the art, the values in Table 3 reflect the number of clock cycles occurring in specific intervals. If such values exceed 31 (the highest value representable by a 5-bit counter), the counter value is augmented with one or more of the state variables ST<4:0>. Thus, counter 302 begins counting from zero in one state, and if it is required to continue counting beyond 31, it is at some point reset to zero and the state machine forced into a different state for the remainder of the counting interval.

As an illustration of the use of state variables to augment the counting range of counter 302, the state machine of FIG. 10 operates in one instance such that when the state machine is in a first state, one PLA term allows counter 302 to count from zero up to 15; if a trailing edge occurs prior to the counter reaching 15, this is interpreted as an error. Another term in PLA 300 provides that if the state machine is in the first state and the counter value reaches 14, the state machine is forced into a second state and the counter is reset. Another PLA term permits the counter to count, while in the second state, up to 13; if a trailing edge is detected prior to the count value reaching 13, this is interpreted as a "0" bit. However, still another term in PLA 300 provides that if the counter value reaches 12 while the state machine is still in the second state, the counter is reset and the state machine is forced to a third state. Using this strategy, the state register is used to "extend" the counter.

Figure 11:
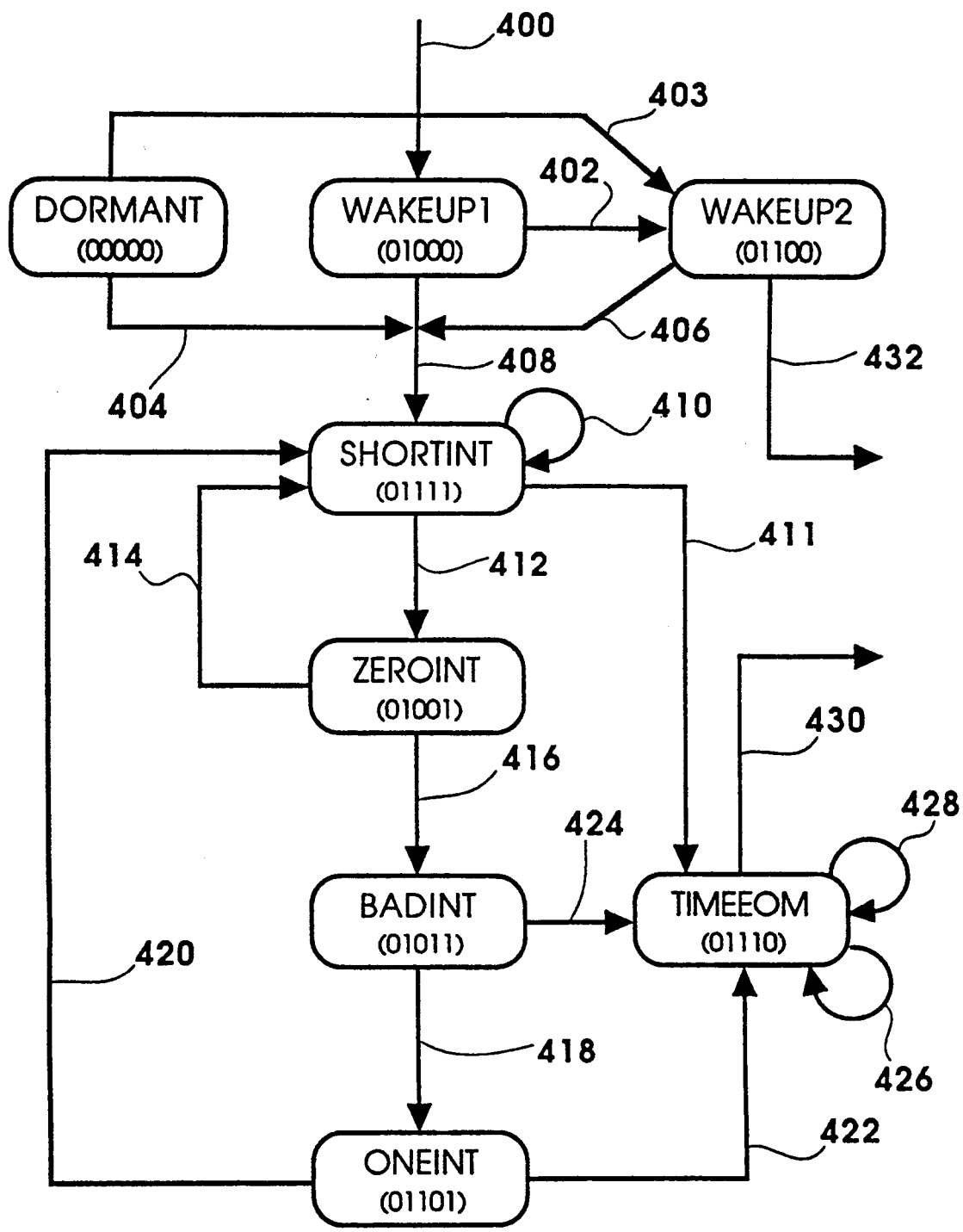
FIG. 11 is a state diagram of the downlink telemetry state machine implemented by the circuit of FIG. 10.
Figure 12:
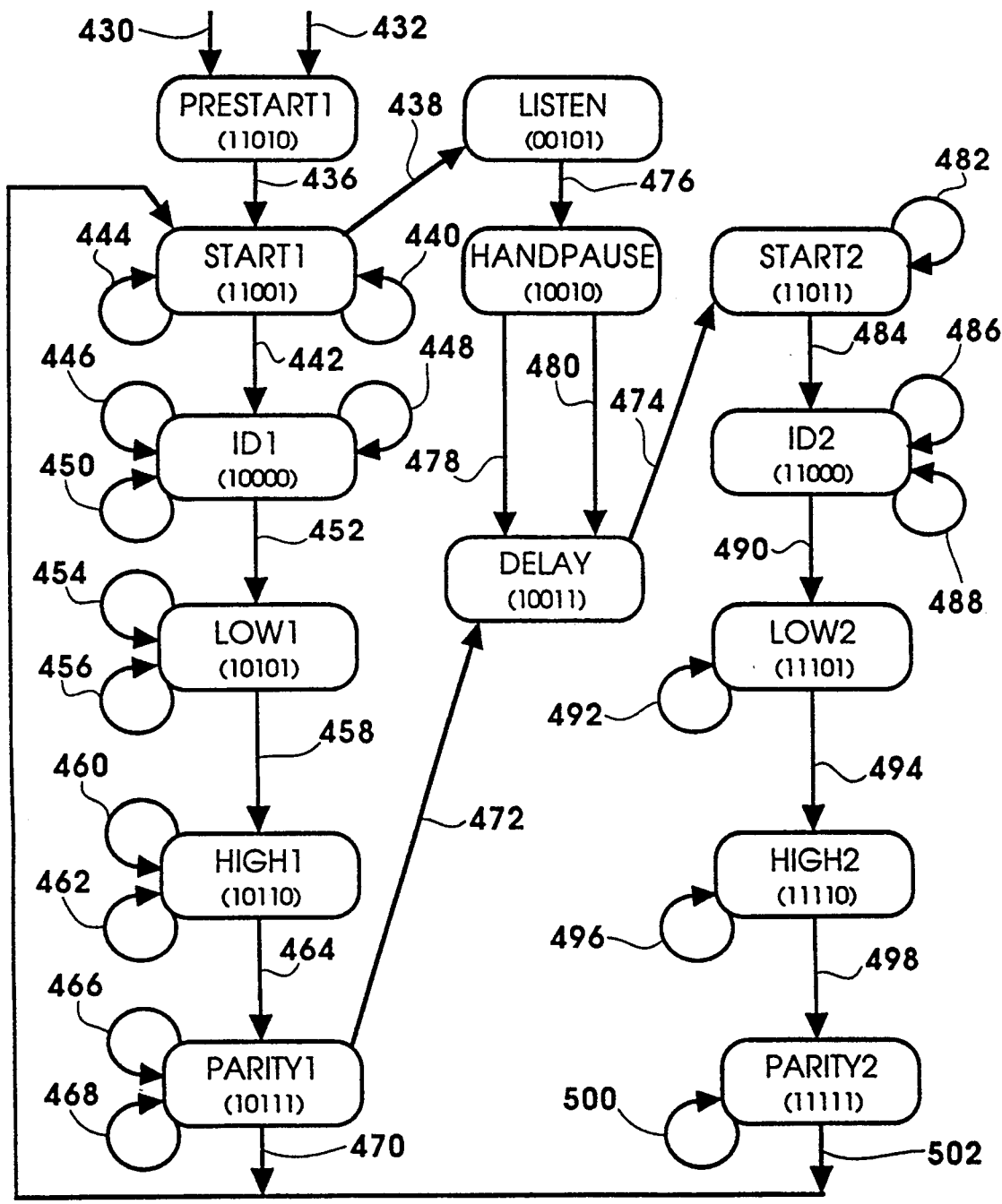
FIG. 12 is a state diagram of the uplink telemetry state machine implemented by the circuit of FIG. 10.

In FIG. 11, there is shown a state diagram illustrating operation of telemetry circuit 33' during downlink telemetry. In FIG. 12, there is shown a state diagram illustrating operation of telemetry circuit 33' during uplink telemetry. As will be appreciated by those of ordinary skill in the art, the state diagrams of FIGS. 11 and 12 show a plurality of states, represented by the various blocks therein, and the possible transitions which can be made from each state, represented by the various arrows therein. The label of each block corresponds to the state name, and the parenthetical number in each block corresponds to the five state variables ST<4:0> for that state.

As will also be appreciated by those of ordinary skill in the art, each transition from a starting state to an ending state in FIGS. 11 and 12 is taken in response to the existence of predetermined conditions when the state machine is in the starting state. Also, when a transition is made, certain actions will be taken by the state machine (i.e., certain outputs from PLA 300 will be asserted).

In the following Table 4, there is set forth a listing of each transition in the state diagrams of FIGS. 11 and 12. For each transition, the column having the heading "Transition No." identifies the reference numeral of a particular state transition in FIG. 11 or 12. The columns under the heading "Starting State" identify the state name and state variable (ST<4:0>) of the starting state for each transition. The columns under the heading "Conditions for Exiting Starting State" identifies the conditions which must exist in order for the state machine to take each transition. The columns under the heading "Target State" identify, for each transition, the state name and state variable of the state that the state machine enters by taking each transition. Finally, the column under the heading "Output Signals Asserted" identifies what output signals from PLA 150 are asserted as a result of taking each transition.

As will be appreciated by those of ordinary skill in the art, any entries of "X" in Table 4 indicate a "don't care" condition. That is, an "X" in a certain signal column of the "Conditions for Exiting Starting State" portion of Table 4 indicates that the state of the corresponding signal is not considered in making the transition.

TABLE 4

| TRANS-ITION NO. | STARTING STATE | | | | | | | CONDITIONS FOR EXITING STARTING STATE | | | | | | |
|---|---|---|---|---|---|---|---|---|---|---|---|---|---|---|
| | STATE NAME | STATE NO. | | | | | | | | | | | | |
| | | ST4 | ST3 | ST2 | ST1 | ST0 | CNT4 | CNT3 | CNT2 | CNT1 | CNT0 | MATCH | PLARF | |
| 400 | ANYTX | 1 | X7 X | X | X | X | X | X | X | X | X | 1 | | |
| 440 | START1 | 1 | 1 | 0 | 0 | 1 | 0 | 0 | 0 | 1 | 1 | X | 0 | |
| 482 | START2 | 1 | 1 | 0 | 1 | 1 | 0 | 0 | 0 | 1 | 1 | X | 0 | |
| 444 | START1 | 1 | 1 | 0 | 0 | 1 | 0 | 1 | 0 | 0 | 0 | X | 0 | |
| 442 | START1 | 1 | 1 | 0 | 0 | 1 | 0 | 1 | 0 | 0 | 0 | X | 0 | |
| 456 | LOW1 | 1 | 0 | 1 | 0 | 1 | X | X | X | X | X | 1 | 0 | |
| 492 | LOW2 | 1 | 1 | 1 | 0 | 1 | X | X | X | X | X | 1 | 0 | |
| 462 | HIGH1 | 1 | 0 | 1 | 1 | 0 | X | X | X | X | X | 1 | 0 | |
| 496 | HIGH2 | 1 | 1 | 1 | 1 | 0 | X | X | X | X | X | 1 | 0 | |
| 468 | PARITY1 | 1 | 0 | 1 | 1 | 1 | X | X | X | X | X | 1 | 0 | |
| 500 | PARITY2 | 1 | 1 | 1 | 1 | 1 | X | X | X | X | X | 1 | 0 | |
| 448 | ID1 | 1 | 0 | 0 | 0 | 0 | X | X | X | X | X | 1 | 0 | |

TABLE 4-continued

| | | | | | | | | | | | | | |
|---|---|---|---|---|---|---|---|---|---|---|---|---|---|
| 450 | ID1 | 1 | 0 | 0 | 0 | 0 | 0 | 0 | 1 | 1 | 1 | X | 0 |
| 446 | ID1 | 1 | 0 | 0 | 0 | 0 | 0 | 0 | 1 | 0 | 1 | X | 0 |
| 488 | ID2 | 1 | 1 | 0 | 0 | 0 | 0 | 0 | 1 | 0 | 1 | X | 0 |
| 452 | ID1 | 1 | 0 | 0 | 0 | 0 | 0 | 1 | 1 | 0 | 0 | X | 0 |
| 454 | LOW1 | 1 | 0 | 1 | 0 | 1 | X | X | X | X | X | 1 | 0 |
| 460 | HIGH1 | 1 | 0 | 1 | 1 | 0 | X | X | X | X | X | 1 | 0 |
| 466 | PARITY1 | 1 | 0 | 1 | 1 | 1 | X | X | X | X | X | 1 | |
| 458 | LOW1 | 1 | 0 | 1 | 0 | 1 | 1 | 0 | 0 | 1 | 1 | X | 0 |
| 438 | START1 | 1 | 1 | 0 | 0 | 1 | 1 | 0 | 1 | 0 | 1 | X | 0 |
| 470 | PARITY1 | 1 | 0 | 1 | 1 | 1 | 1 | 0 | 1 | 0 | 1 | X | 0 |
| 502 | PARITY2 | 1 | 1 | 1 | 1 | 1 | 1 | 0 | 1 | 0 | 1 | X | 0 |
| 464 | HIGH1 | 1 | 0 | 1 | 1 | 0 | 1 | 0 | 0 | 1 | 1 | X | 0 |
| 472 | PARITY1 | 1 | 0 | 1 | 1 | 1 | 1 | 0 | 0 | 1 | 0 | X | 0 |
| 474 | DELAY | 1 | 0 | 0 | 1 | 1 | 0 | 0 | 0 | 1 | 0 | X | 0 |
| 484 | START2 | 1 | 1 | 0 | 1 | 1 | 0 | 1 | 0 | 0 | 0 | X | 0 |
| 490 | ID2 | 1 | 1 | 0 | 0 | 0 | 0 | 1 | 1 | 0 | 0 | X | 0 |
| 494 | LOW2 | 1 | 1 | 1 | 0 | 1 | 1 | 0 | 0 | 1 | 1 | X | 0 |
| 498 | HIGH2 | 1 | 1 | 1 | 1 | 0 | 1 | 0 | 0 | 1 | 1 | X | 0 |
| 486 | ID2 | 1 | 1 | 0 | 0 | 0 | 0 | 1 | 0 | 0 | 1 | X | 0 |
| 428 | TIMEEOM | 0 | 1 | 1 | 1 | 0 | X | X | X | X | X | X | 1 |
| 476 | LISTEN | 0 | 0 | 1 | 0 | 1 | 1 | 1 | 0 | 1 | 0 | X | X |
| 478 | HANDPAUSE | 1 | 0 | 0 | 1 | 0 | 1 | 1 | 1 | 1 | 1 | X | 0 |
| 480 | HANDPAUSE | 1 | 0 | 0 | 1 | 0 | 1 | 1 | 1 | 1 | 1 | X | 0 |
| 402 | WAKEUP1 | 0 | 1 | 0 | 0 | 0 | 1 | 1 | 1 | 1 | 1 | X | 0 |
| 408 | WAKEUP1 | 0 | 1 | 0 | 0 | 0 | X | X | X | X | X | X | 1 |
| 432 | WAKEUP2 | 0 | 1 | 1 | 0 | 0 | 1 | 1 | 1 | 1 | 1 | X | 0 |
| 412 | SHORTINT | 0 | 1 | 1 | 1 | 1 | 0 | 1 | 1 | 1 | 0 | X | 0 |
| 411 | SHORTINT | 0 | 1 | 1 | 1 | 1 | X | X | X | X | X | X | 1 |
| 424 | BADINT | 0 | 1 | 0 | 1 | 1 | X | X | X | X | X | X | 1 |
| 414 | ZEROINT | 0 | 1 | 0 | 0 | 1 | X | X | X | X | X | X | 1 |
| 416 | ZEROINT | 0 | 1 | 0 | 0 | 1 | 0 | 1 | 1 | 0 | 0 | X | 0 |
| 418 | BADINT | 0 | 1 | 0 | 1 | 1 | 0 | 0 | 0 | 1 | 1 | X | 0 |
| 420 | ONEINT | 0 | 1 | 1 | 0 | 1 | X | X | X | X | X | X | 1 |
| 422 | ONEINT | 0 | 1 | 1 | 0 | 1 | 0 | 1 | 1 | 0 | 1 | X | 0 |
| 426 | TIMEEOM | 0 | 1 | 1 | 1 | 0 | 1 | 0 | 0 | 0 | 0 | X | 0 |
| 430 | TIMEEOM | 0 | 1 | 1 | 1 | 0 | X | X | X | X | X | X | X |
| 410 | SHORTINT | 0 | 1 | 1 | 1 | 1 | 0 | 0 | 0 | 0 | 0 | X | 0 |
| 436 | PRESTART1 | 1 | 1 | 0 | 1 | 0 | X | X | X | X | X | X | 0 |
| 403 | DORMANT | 0 | 0 | 0 | 0 | 0 | 1 | 1 | 1 | 1 | 1 | X | 0 |
| 404 | DORMANT | 0 | 0 | 0 | 0 | 0 | X | X | X | X | X | X | 1 |

| TRANS-ITION NO. | CONDITIONS FOR EXITING STARTING STATE | | | TARGET STATE | | | | | | OUTPUT SIGNALS ASSERTED | | | |
|---|---|---|---|---|---|---|---|---|---|---|---|---|---|
| | SROUT | FRHI | FRLO | STATE NAME | TO4 | TO3 | TO2 | TO1 | TO0 | TXD | SHIFT | SRDATA | LOAD |
| 400 | X | X | X | WAKEUP1 | 0 | 1 | 0 | 0 | 0 | 0 | 0 | 1 | 1 |
| 400 | X | X | X | START1 | 1 | 1 | 0 | 0 | 1 | 1 | 0 | 0 | 0 |
| 482 | X | X | X | START2 | 1 | 1 | 0 | 1 | 1 | 1 | 0 | 0 | 0 |
| 444 | 1 | 1 | 0 | START1 | 1 | 1 | 0 | 0 | 1 | 1 | 0 | 0 | 0 |
| 442 | 0 | X | X | ID1 | 1 | 0 | 0 | 0 | 0 | 0 | 0 | 0 | 0 |
| 456 | X | 1 | X | LOW1 | 1 | 0 | 1 | 0 | 1 | 1 | 0 | 0 | 0 |
| 492 | X | X | X | LOW2 | 1 | 1 | 1 | 0 | 1 | 1 | 0 | 0 | 0 |
| 462 | X | 1 | X | HIGH1 | 1 | 0 | 1 | 1 | 0 | 1 | 0 | 0 | 0 |
| 496 | X | X | X | HIGH2 | 1 | 1 | 1 | 1 | 0 | 1 | 0 | 0 | 0 |
| 468 | X | 1 | X | PARITY1 | 1 | 0 | 1 | 1 | 1 | 1 | 0 | 0 | 0 |
| 500 | X | X | X | PARITY2 | 1 | 1 | 1 | 1 | 1 | 1 | 0 | 0 | 0 |
| 448 | X | 0 | 1 | ID1 | 1 | 0 | 0 | 0 | 0 | 1 | 0 | 0 | 0 |
| 450 | X | 1 | 0 | ID1 | 1 | 0 | 0 | 0 | 0 | 1 | 0 | 0 | 0 |
| 446 | X | 1 | 1 | ID1 | 1 | 0 | 0 | 0 | 0 | 1 | 0 | 0 | 0 |
| 488 | X | 1 | 1 | ID2 | 1 | 1 | 0 | 0 | 0 | 1 | 0 | 0 | 0 |
| 452 | X | X | X | LOW1 | 1 | 0 | 1 | 0 | 1 | 0 | 0 | 0 | 0 |
| 454 | X | 0 | 1 | LOW1 | 1 | 0 | 1 | 0 | 1 | 1 | 0 | 0 | 0 |
| 460 | X | 0 | 1 | HIGH1 | 1 | 0 | 1 | 1 | 0 | 1 | 0 | 0 | 0 |
| 466 | X | 0 | 1 | PARITY1 | 1 | 0 | 1 | 1 | 1 | 1 | 0 | 0 | 0 |
| 458 | X | X | X | HIGH1 | 1 | 0 | 1 | 1 | 0 | 0 | 0 | 0 | 0 |
| 438 | 1 | X | X | LISTEN | 0 | 0 | 1 | 0 | 1 | 0 | 0 | 0 | 0 |
| 470 | X | X | X | START1 | 1 | 1 | 0 | 0 | 1 | 1 | 0 | 0 | 1 |
| 502 | X | X | X | START1 | 1 | 1 | 0 | 0 | 1 | 1 | 0 | 0 | 1 |
| 464 | X | X | X | PARITY1 | 1 | 0 | 1 | 1 | 1 | 0 | 0 | 0 | 0 |
| 472 | X | 1 | 1 | DELAY | 1 | 0 | 0 | 1 | 1 | 0 | 0 | 0 | 0 |
| 474 | X | X | X | START2 | 1 | 1 | 0 | 1 | 1 | 1 | 0 | 0 | 0 |
| 484 | X | X | X | ID2 | 1 | 1 | 0 | 0 | 0 | 0 | 0 | 0 | 0 |
| 490 | X | X | X | LOW2 | 1 | 1 | 1 | 0 | 1 | 0 | 0 | 0 | 0 |
| 494 | X | X | X | HIGH2 | 1 | 1 | 1 | 1 | 0 | 0 | 0 | 0 | 0 |
| 498 | X | X | X | PARITY2 | 1 | 1 | 1 | 1 | 1 | 0 | 0 | 0 | 0 |
| 486 | X | 1 | 0 | ID2 | 1 | 1 | 0 | 0 | 0 | 1 | 0 | 0 | 0 |
| 428 | 0 | X | X | TIMEEOM | 0 | 1 | 1 | 1 | 0 | 0 | 0 | 1 | 1 |
| 476 | X | X | X | HANDPAUSE | 1 | 0 | 0 | 1 | 0 | 0 | 0 | 0 | 0 |
| 478 | 0 | X | X | DELAY | 1 | 0 | 0 | 1 | 1 | 0 | 1 | 1 | 0 |
| 480 | 1 | X | X | DELAY | 1 | 0 | 0 | 1 | 1 | 0 | 1 | 0 | 0 |
| 402 | X | X | X | WAKEUP2 | 0 | 1 | 1 | 0 | 0 | 0 | 0 | 0 | 0 |
| 408 | X | X | X | SHORTINT | 0 | 1 | 1 | 1 | 1 | 0 | 0 | 1 | 1 |

TABLE 4-continued

| 432 | X | X | X | PRESTART1 | 1 | 1 | 0 | 1 | 0 | 0 | 0 | 0 | 0 |
|---|---|---|---|---|---|---|---|---|---|---|---|---|---|
| 412 | X | X | X | ZEROINT | 0 | 1 | 0 | 0 | 1 | 0 | 0 | 0 | 0 |
| 411 | X | X | X | TIMEEOM | 0 | 1 | 1 | 1 | 0 | 0 | 0 | 1 | 1 |
| 424 | X | X | X | TIMEEOM | 0 | 1 | 1 | 1 | 0 | 0 | 0 | 1 | 1 |
| 414 | X | X | X | SHORTINT | 0 | 1 | 1 | 1 | 1 | 0 | 1 | 0 | 0 |
| 416 | X | X | X | BADINT | 0 | 1 | 0 | 1 | 1 | 0 | 0 | 0 | 0 |
| 418 | X | X | X | ONEINT | 0 | 1 | 1 | 0 | 1 | 0 | 0 | 0 | 0 |
| 420 | X | X | X | SHORTINT | 0 | 1 | 1 | 1 | 1 | 0 | 1 | 1 | 0 |
| 422 | X | X | X | TIMEEOM | 0 | 1 | 1 | 1 | 0 | 0 | 0 | 1 | 1 |
| 426 | 0 | X | X | TIMEEOM | 0 | 1 | 1 | 1 | 0 | 0 | 1 | 1 | 0 |
| 430 | 1 | X | X | PRESTART1 | 1 | 1 | 0 | 1 | 0 | 0 | 0 | 1 | 1 |
| 410 | 1 | X | X | SHORTINT | 0 | 1 | 1 | 1 | 1 | 0 | 0 | 1 | 1 |
| 436 | X | X | X | START1 | 1 | 1 | 0 | 0 | 1 | 1 | 0 | 0 | 1 |
| 403 | X | X | X | WAKEUP2 | 0 | 1 | 1 | 0 | 0 | 0 | 0 | 0 | 0 |
| 404 | X | X | X | SHORTINT | 0 | 1 | 1 | 1 | 1 | 0 | 0 | 1 | 1 |

Referring to FIG. 11 and to Table 4, circuit 33' enters the downlink telemetry mode of operation via a transition designated with reference numeral 400. It is to be understood that transition 400 may be taken from any uplink telemetry state in FIG. 12, whenever the signal PLARF is asserted. For a valid downlink telemetry signal, the PLARF signal will be asserted a first time in response to wakeup burst detector circuit 308 detecting a wake-up pulse in the received RF pulse stream.

Transition 400 puts the state machine in the WAKEUP1 state. From the WAKEUP1 state, the state machine takes transition 408 to the SHORTINT state when PLARF is asserted (i.e., upon detection of the trailing edge of the wake-up burst). In the SHORTINT state, counter 302 is enabled, and begins counting clock cycles. From the SHORTINT state, the state machine will enter the ZEROINT state via transition 412 only if counter 302 reaches a count value of 14 (CNT<5:0>={0 1110} before PLARF is asserted again indicating the trailing edge of a data burst. If counter 302 is unable to reach 14 before PLARF is asserted, this indicates that the trailing-edge to trailing-edge interval between the wake-up burst and the first data burst was too short to constitute a zero bit encoding. In this instance the transition 411 will be taken, ending the telemetry session as a result of the error in transmission.

If counter 302 does reach a count value of 14 prior to PLARF being asserted, counter 302 is reset and the state machine takes transition 412 to the ZEROINT state. In the ZEROINT state, counter 302 begins counting from zero, and will take transition 416 to BADINT only if counter 302 reaches a value of 12 prior to PLARF being asserted. If the bit being transmitted is a "0", however, PLARF will be asserted before counter 302 reaches a count value of 12 in the ZEROINT state, since a trailing edge will be detected between 16 and 28 clock cycles following the last trailing edge for a zero (see Table 3 above).

If a trailing edge is detected in the appropriate window corresponding to a "0" bit, the state machine will take transition 414 to the SHORTINT state, thus beginning the counting of the next trailing-edge to trailing-edge interval. As transition 414 is taken, assertion of the SHIFT output signal from PLA 300 will cause a zero to be shifted into shift register 306.

If the data bit being transmitted is a "1", however, counter 302 will reach a count value of 12 in the ZEROINT state prior to PLARF being asserted. Thus, the state machine will take transition 416 to the BADINT state. If an interval too short to be a "1" but too long to be a "0" is present, PLARF will be asserted before counter 302 can reach a count value of 3 in the BADINT state, and transition 424 will be taken, ending the telemetry session as a result of the error in transmission.

If a "1" is being transmitted, counter 302 will reach a count value of 13 in the BADINT state prior to assertion of PLARF; thus, the state machine will take transition 418 to the ONEINT state. In the ONEINT state, if counter 302 reaches a count value of 13 prior to PLARF being asserted, this indicates a trailing-edge to trailing-edge interval longer than allowed for a "1", and transition 422 will be taken to end the telemetry session.

If a "1" is being transmitted, counter 302 will not reach a value of 13 in the ONEINT state prior to PLARF being asserted. This causes the state machine to take transition 420 back to the SHORTINT state to begin counting for the next trailingedge to trailing-edge interval. As transition 420 is taken PLA 300 asserts the SHIFT and SRDATA output signals, thereby causing a "1" to be shifted into shift register 306.

For uplink telemetry, circuit 33' begins in the PRESTART1 state, having entered that state either on transition 430 from the TIMEEOM downlink state, or on transition 432 from the WAKEUP2 downlink state.

From the PRESTART1 state, the state machine takes transition 436 to enter the START1 state, as long as PLARF is not asserted. When taking transition 436. PLA 300 asserts the TELEMETRY OUT (TXD) output signal, thereby transmitting the first sychronization pulse (that is, the pulse in time slot 1 of each uplink telemetry frame—see FIG. 7). In the START1 state, the state machine takes transition 440 when counter 302 reaches a count value of three. When taking transition 440, PLA 300 asserts the TELEMETRY OUT (TXD) signal, thereby causing the second synchronization pulse (the pulse in time slot 4 of each uplink telemetry frame). Still in the START1 state, the state machine will take transition 442 upon counter 302 reaching a count value of eight. Thus, the state machine enters the state ID1, to transmit the channel ID value, the channel ID section 200 of each uplink telemetry frame beginning in time slot 9 (see FIG. 7).

After transmitting the channel ID, the state machine will take transition 452 to the LOW1 state, from which state the low-order nibble of data is transmitted. From the LOW1 state, the state machine will take either transition 454 or transition 456 (depending upon the status of the frame identifying signals FRHI and FRLO), transmitting an RF pulse in either case upon assertion of the MATCH signal from comparator 326. Due to the current state variable in the LOW1 state (two bits of which are applied to the select input of comparator 326), comparator 326 is controlled to compare the low-order nibble of the data in shift register 306 to the count value, so that an RF pulse will be transmitted in the time slot corresponding to the pulse-position modulation of the low-order nibble.

After transmitting the low-order data nibble from the LOW1 state, the state machine will take transition 458 to the HIGH1 state when counter 302 reaches a count value of nineteen. (A count value of nineteen is used to take into account the four time-slot gap between the low order nibble section 202 and the high order nibble section 204 of an uplink telemetry frame, as shown in FIG. 7).

In the HIGH1 state, the state machine will take either transition 460 or transition 462 (depending upon the status of the frame identifying signals FRHI and FRLO) to transmit an RF pulse upon assertion of the MATCH output from comparator 326. In the HIGH1 state, the state variable applied to the select input of comparator 326 controls comparator 326 to compare the high-order nibble of the shift register data to the counter value, so that the MATCH signal is asserted in the appropriate time slot of the high-order nibble section 204 of the uplink frame. That is, a telemetry pulse is transmitted in a time slot within high-order nibble section 204 corresponding to the particular high-order nibble being transmitted.

As will be appreciated by those of ordinary skill in the art, the abovedescribed operation of comparator 326 in comparing the respective nibbles of the uplink data to the count value eliminates the necessity of providing a RAM-programmable section in PLA 300, as was done in the previously disclosed embodiment of FIG. 2.

After transmitting the high-order nibble from state HIGH1, the state machine will take transition 464 to the PARITY1 state, for transmission of parity information.

From the foregoing detailed description of specific embodiments of the invention, it should be apparent that a versatile and efficient telemetry system has been disclosed. Although particular embodiments of the invention have been described hereinabove in some detail, this has been done for the purposes of illustrating the underlying principles of the present invention, and is not intended to be limiting with respect to the scope of the present invention. It is contemplated by the inventors that numerous design options may be exercised in the practicing of the present invention, and that various substitutions, alterations, and modifications may be made to the embodiments disclosed herein without departing from the spirit and scope of the present invention as defined in the appended claims.

In particular, it is a notable feature of the present invention that the use of a programmable device (i.e., a PLA) in the telemetry system enables the system to be readily adapted for use with different types of telemetry protocols. Thus, the practice of the present invention is not limited to pulse-interval or pulse-position modulation as in the examples described herein.

What is claimed is:

1. A telemetry system for communicating digital information via a radio-frequency signal, comprising:
    an antenna, adapted to receive said radio-frequency signal;
    an RF detect circuit, coupled to said antenna and responsive to said radio frequency signal to convert said radio-frequency signal into a digital pulse stream;
    a clock, responsive to assertion of a clock activation signal to produce a clock signal at a clock output terminal thereof;
    a clock activation circuit, coupled to said RF detect circuit to receive said digital pulse stream, and coupled to said clock, said clock activation circuit responsive to a first predetermined characteristic of said digital pulse stream to assert said clock activation signal, and responsive to a second predetermined characteristic of said digital pulse stream to deassert said clock activation signal;
    a counter, coupled to said clock output terminal and adapted to present a plurality of count value output signals representing said counter's count value at a plurality of output terminals thereof, said counter responsive to a cycle of said clock signal to increment said count value;
    a logic array, coupled to said counter output terminals to receive said count value output signals, and coupled to said RF detect circuit to receive said digital pulse stream, said logic array responsive to a first predetermined combination of said counter value output signals and said digital pulse stream to assert a first output signal indicative of a digital "1" encoded into said radio-frequency signal, said logic array responsive to a second predetermined combination of said counter value output signals and said digital pulse stream to assert a second output signal indicative of a digital "0" encoded into said radio-frequency signal.

2. A telemetry system in accordance with claim 1, wherein said first predetermined characteristic of said pulse stream comprises a trailing edge therein.

3. A telemetry system in accordance with claim 2, wherein said second predetermined characteristic of said pulse stream comprises a trailing edge therein.

4. A telemetry system in accordance with claim 1, wherein said logic array has a plurality of state variable output terminals for presenting state variable signals thereon, a plurality of state variable input terminals for receiving state variable signals thereon, and a telemetry out terminal for presenting a telemetry out signal thereon, said telemetry system further comprising:
    a state register comprising a plurality of bit storage locations, said state register having a plurality of input terminals coupled to said logic array state variable output terminals and further having a plurality of output terminals coupled to said logic array state variable input terminals;
    a data register, adapted to store a plurality of bits to be encoded into a radio frequency signal, said data register having a plurality of output terminals for presenting signals thereon corresponding to said stored bits;
    a comparator, coupled to said data register output terminals and to said counter output terminals, said comparator having a comparator output terminal coupled to an input of said logic array, said comparator responsive to a match between said plurality of stored bits and said count value signals to assert a signal on said comparator output terminal, wherein said logic array is responsive to assertion of said signal on said comparator output terminal to assert said telemetry out signal.

5. A telemetry system in accordance with claim 4, further comprising:
    a telemetry driver circuit, having an input coupled to said logic array to receive said telemetry out signal and an output coupled to said antenna, said telemetry driver circuit responsive to assertion of said telemetry out signal to deliver a pulse to said antenna such that a radio-frequency burst is transmitted.

6. A telemetry system for receiving and decoding digital data encoded in a radio-frequency signal, comprising:
- a telemetry coil, adapted to receive said radio-frequency signal;
- a detector circuit, coupled to said coil and responsive to a first predetermined characteristic in said received radio-frequency signal to assert a wakeup signal and thereafter responsive to a second predetermined characteristic in said received radio-frequency signal to assert a detect signal;
- a clock, coupled to said detector circuit and responsive to assertion of said detect signal to produce a clock signal;
- a counter, coupled to said clock to receive said clock signal, and coupled to said detector circuit to receive said detect signal, said counter having a plurality of output terminals for presenting a count value thereon, said counter responsive to said clock signal to said detect signal to reset said count value and to count clock cycles of said clock signal;
- a programmed logic array, having a first plurality of input terminals coupled to said counter output terminals to receive said count value, said logic array further having a plurality of output terminals, said logic array responsive to a first predetermined count value to assert a signal on a first one of said plurality of output terminals and responsive to a second predetermined count value to assert a signal on a second one of said plurality of output terminals;
- a first decoding circuit, coupled to said detector circuit and to said logic array, said first decoding circuit responsive to said received signal and to assertion of said signal on said first logic array output terminal to assert a first decoder output signal;
- a second decoding circuit, coupled to said detector circuit and to said logic array, said second decoding circuit responsive to said received signal and to assertion of said signal on said second logic array output terminal to assert a second decoder output signal;
- a digital data storage circuit, coupled to said first and second decoding circuits and responsive to assertion of said first decoder output signal to store a binary "0" bit and responsive to assertion of said second decoder output signal to store a binary "1" bit.

7. A system in accordance with claim 6, wherein said radio-frequency signal comprises a radio-frequency pulse stream.

8. A system in accordance with claim 7, wherein said first predetermined characteristic in said received radio-frequency signal comprises a radio-frequency pulse having a duration of at least a predetermined interval.

9. A system in accordance with claim 7, wherein said second predetermined characteristic in said received radio-frequency signal comprises a trailing edge of a radio-frequency pulse.

10. A system in accordance with claim 6, wherein said digital data is pulse interval modulated in said radio-frequency signal.

11. A system in accordance with claim 6, wherein said digital data is pulse width modulated in said radio-frequency signal.

12. A telemetry system for transmitting digital data encoded in a radio-frequency signal, comprising:
- a telemetry coil, responsive to a telemetry driver signal to transmit a radio frequency burst;
- a telemetry driver circuit, having an output terminal coupled to said coil and having an input terminal, said telemetry driver circuit responsive to assertion of a signal at said input terminal to apply said telemetry driver signal to said coil;
- a digital memory circuit, adapted to store said digital data;
- a clock, having an enable input terminal and a clock output terminal, said clock responsive to assertion of an uplink enable signal applied to said enable input terminal to produce a clock signal at said clock output terminal;
- a counter having a plurality of output terminals and further having a clock input terminal coupled to said clock output terminal, said counter responsive to said clock signal on said clock output terminal to count clock cycles therein, said counter adapted to present a clock cycle count value on said output terminals;
- a state register comprising a plurality of bit storage locations, said state register having a plurality of state input terminals, a clock input terminal coupled to said clock output terminal, and a plurality of state output terminals, said state register responsive to a cycle of said clock signal to store, in said plurality of bit storage locations, data corresponding to signals applied to said state input terminals;
- a RAM-programmable logic array having a first plurality of input terminals coupled to said counter output terminals, a second plurality of input terminals coupled to said state register state output terminals, and at least one output terminal coupled to said telemetry driver circuit input terminal, said logic array coupled to said digital memory circuit and responsive to said data stored in said digital memory circuit to program an output term such that said logic array is responsive to a match between said count value applied to said first plurality of input terminals and signals on said state output terminals, on the one hand, and said digital data, on the other hand, to assert a signal at said output terminal.

13. A telemetry system in accordance with claim 12, wherein said digital data is pulse position modulated in said radio frequency signal.

14. A telemetry system for transmitting an uplink radio-frequency signal having uplink digital data encoded therein and for receiving and decoding downlink digital data encoded in a downlink radio-frequency signal, said telemetry system comprising:
- a telemetry coil, adapted to receive said downlink radio-frequency signal;
- a detector circuit, coupled to said coil and responsive to a first predetermined characteristic in said downlink radio-frequency signal to assert a wakeup signal and responsive to assertion of said wake-up signal and a second predetermined characteristic in said downlink radio-frequency signal to assert a detect signal;
- a clock, having an enable input coupled to said detector circuit to receive said detect signal, said clock responsive to assertion of said detect signal at said enable input to produce a clock signal;

a counter, coupled to said clock to receive said clock signal, said counter responsive to said clock signal to count clock cycles therein, said counter having a plurality of output terminals for presenting a count value thereon;

a programmed logic array, having a first plurality of input terminals coupled to said counter output terminals to receive said count value, said logic array further having a plurality of output terminals, said logic array responsive to a first predetermined count value to assert a signal on a first one of said plurality of output terminals and responsive to a second predetermined count value to assert a signal on a second one of said plurality of output terminals;

a first decoding circuit, coupled to said detector circuit and to said logic array, said first decoding circuit responsive to said downlink signal and to assertion of said signal on said first logic array output terminal to assert a first decoder output signal;

a second decoding circuit, coupled to said detector circuit and to said logic array, said second decoding circuit responsive to said downlink signal and to assertion of said signal on said second logic array output terminal to assert a second decoder output signal;

a digital data storage circuit, coupled to said first and second decoding circuits and responsive to assertion of said first decoder output signal to store a binary "0" bit and responsive to assertion of said second decoder output signal to store a binary "1" bit;

a telemetry driver circuit, having an output terminal coupled to said coil and having an input terminal, said telemetry driver circuit responsive to assertion of a signal at said input terminal to apply said telemetry driver signal to said coil;

an uplink control circuit, having an uplink data output terminal and an uplink enable output terminal, said uplink output terminal coupled to said clock enable signal such that said clock is responsive to assertion of a signal on said uplink enable output terminal to present said clock signal on said clock output terminal;

a digital memory circuit, adapted to store said uplink data presented on said uplink data output terminal;

a state register comprising a plurality of bit storage locations, said state register having a plurality of state input terminals, a clock input terminal coupled to said clock output terminal, and a plurality of state output terminals, said state register responsive to a cycle of said clock signal to store, in said plurality of bit storage locations, data corresponding to signals applied to said state input terminals;

said logic array having further having a second plurality of input terminals coupled to said state register state output terminals, and at least one output terminal coupled to said telemetry driver circuit input terminal, said logic array coupled to said digital memory circuit and responsive to said data stored in said digital memory circuit to program an output term such that said logic array is responsive to a match between said count value applied to said first plurality of input terminals and signals on said state output terminals, on the one hand, and said digital data, on the other hand, to assert a signal at said output terminal.

15. A system in accordance with claim 14, wherein said uplink and downlink radio-frequency signals comprise radio-frequency pulse streams.

16. A system in accordance with claim 15, wherein said first predetermined characteristic in said downlink radio-frequency signal comprises a radio-frequency pulse having a duration of at least a predetermined interval.

17. A system in accordance with claim 15, wherein said second predetermined characteristic in said downlink radio-frequency signal comprises a trailing edge of a radio-frequency pulse.

18. A system in accordance with claim 14, wherein said downlink digital data is pulse interval modulated in said downlink radio-frequency signal.

19. A system in accordance with claim 14, wherein said downlink digital data is pulse width modulated in said downlink radio-frequency signal.

20. A system in accordance with claim 14, wherein said uplink digital data is pulse position modulated in said uplink radio-frequency signal.

21. A telemetry system for transmitting an uplink radio-frequency signal having uplink digital data encoded therein and for receiving and decoding downlink digital data encoded in a downlink radio-frequency signal, said telemetry system comprising:

a telemetry coil, adapted to receive said downlink radio-frequency signal;

a detector circuit, coupled to said coil and responsive to a first predetermined characteristic in said downlink radio-frequency signal to assert a wake up signal and responsive to a second predetermined characteristic in said downlink radio-frequency signal to assert a detect signal;

a clock, having a clock output terminal, said clock adapted to produce a clock signal at said clock output terminal;

a counter, coupled to said clock output terminal to receive said clock signal, said counter responsive to said clock signal to count clock cycles therein, said counter having a plurality of output terminals for presenting a count value thereon;

a logic array, having:
 a first plurality of input terminals coupled to said counter output terminals to receive said count value;
 a detect input coupled to said detector circuit to receive said detect signal;
 a match input;
 a downlink data output terminal for presenting a downlink data output signal thereon; and
 a store output terminal for presenting a store output signal; said logic array responsive to a first predetermined count value presented on said counter output terminals concurrently with assertion of said detect signal to deassert said downlink data output signal and to assert said store output signal, and responsive to a second predetermined count value presented on said counter output terminals concurrently with assertion of said detect signal to assert said downlink data output signal and said store output signal;

a digital data storage circuit, coupled to said downlink data output terminal and to said store output terminal, said storage circuit responsive to assertion of said store signal to store a binary "0" bit when said downlink data signal is deasserted and to store a binary "1" bit when said downlink data signal is asserted;

a telemetry driver circuit, having an output terminal coupled to said coil and having an input terminal, said telemetry driver circuit responsive to assertion of a signal at said input terminal to apply said telemetry driver signal to said coil;

a state register comprising a plurality of bit storage locations, said state register having a plurality of state input terminals, a clock input terminal coupled to said clock output terminal, and a plurality of state output terminals, said state register responsive to a cycle of said clock signal to store, in said plurality of bit storage locations, state data corresponding to signals applied to said state input terminals;

a comparator circuit, having input terminals coupled to said counter output terminals and to said data storage circuit, and having a match output terminal coupled to said logic array match input, said comparator circuit responsive to a match between said count value and data stored in said storage circuit to assert a signal on said match output terminal;

said logic array having further having a second plurality of input terminals coupled to said state register state output terminals, and a telemetry out output terminal coupled to said telemetry driver circuit input terminal, said logic array responsive to assertion of said match signal and a predetermined combination of said state data to assert a signal at said telemetry out output terminal.

22. A telemetry system for receiving and decoding downlink digital data encoded in a downlink telemetry signal, and for encoding and transmitting uplink digital data in an uplink telemetry signal, said telemetry system comprising:

a telemetry coil, adapted to receive said downlink telemetry signal, and to transmit said uplink telemetry signal in accordance with a telemetry driver signal;

a telemetry driver circuit having an input terminal and an output terminal coupled to said telemetry coil, said driver circuit responsive to a telemetry out signal applied to said telemetry driver input terminal to present said telemetry driver signal on said telemetry driver output terminal;

a detector circuit coupled to said telemetry coil to receive said downlink telemetry signal therefrom, said detector circuit having a detect output terminal, said detector circuit responsive to a predetermined characteristic in said downlink signal to assert a detect output signal on said detect output terminal;

a clock, having a clock output terminal for presenting a clock output signal thereon;

a counter, having a clock input terminal coupled to said clock output terminal, said counter having a plurality of counter output terminals for presenting a count value thereon, said counter responsive to cycles of said clock signal to increment said count value;

a state register, having a plurality of bit storage locations therein, said state register having a plurality of state input terminals and a plurality of state output terminals;

a data storage circuit comprising a plurality of bit storage locations, said data storage circuit having a store input terminal and a data input terminal for receiving a data input signal, said data storage circuit responsive to assertion of said store input to store data corresponding to said data input signal;

a comparator circuit, having a match output terminal, and further having a first plurality of input terminals coupled to said data storage circuit and a second plurality of input terminals coupled to said counter output terminals, said comparator circuit responsive to a match between uplink telemetry data stored in said data storage circuit and said counter value to assert a signal on said match output terminal;

a logic array, having:
  a plurality of logic array state input terminals coupled to said state register state output terminals;
  a plurality of logic array state output terminals coupled to said state register state input terminals;
  a plurality of counter input terminals coupled to said counter output terminals;
  a detect input terminal coupled to said detect output terminal;
  a match input terminal coupled to said comparator match output terminal;
  a downlink telemetry output terminal, coupled to said telemetry driver circuit input terminal to present said telemetry out signal thereto;
  an uplink telemetry output terminal, coupled to said telemetry driver input terminal;
  a store output terminal, coupled to said store input terminal of said data storage circuit;
wherein said logic array is responsive to a first predetermined combination of signals applied to said state input terminals, counter input terminals, detect input terminal and match input terminal to assert signals on said store and said downlink telemetry output terminals, and wherein said logic array is responsive to a second predetermined combination of signals applied to said state input terminals, counter input terminals, detect input terminal, and match input terminal to assert a signal on said uplink telemetry output terminal.

23. A telemetry system for communicating digital information via a radio-frequency signal, comprising:

an antenna, adapted to receive said radio-frequency signal;

an RF detect circuit, coupled to said antenna and responsive to said radio frequency signal to convert said radio-frequency signal into a digital pulse stream;

a counting circuit, coupled to said RF detect circuit to receive said digital pulse stream, said counting circuit adapted to present a plurality of count value output signals representing a count value at a plurality of output terminals thereof, said counting circuit responsive to a first predetermined characteristic of said digital pulse stream to begin incrementing said count value at a predetermined rate and responsive to a second predetermined characteristic of said digital pulse stream to cease incrementing said counter value;

a logic array, coupled to said counting circuit output terminals to receive said count value output signals, and coupled to said RF detect circuit to receive said digital pulse stream, said logic array responsive to a first predetermined combination of said counter value output signals and said digital pulse stream to assert a first output signal indicative of a digital "1" encoded into said radio-frequency signal, said logic array responsive to a second predetermined combination of said counter value output signals and said digital pulse stream to assert a second output signal indicative of a digital "0" encoded into said radio-frequency signal.

24. A telemetry system in accordance with claim 23, wherein said first predetermined characteristic of said pulse stream comprises a trailing edge therein.

25. A telemetry system in accordance with claim 24, wherein said second predetermined characteristic of said pulse stream comprises a trailing edge therein.

26. A telemetry system in accordance with claim 23, wherein said logic array has a plurality of state variable output terminals for presenting state variable signals thereon, a plurality of state variable input terminals for receiving state variable signals thereon, and a telemetry out terminal for presenting a telemetry out signal thereon, said telemetry system further comprising:
- a state register comprising a plurality of bit storage locations, said state register having a plurality of input terminals coupled to said logic array state variable output terminals and further having a plurality of output terminals coupled to said logic array state variable input terminals;
- a data register, adapted to store a plurality of bits to be encoded into a radio-frequency signal, said data register having a plurality of terminals for presenting signals thereon corresponding to said stored bits;
- a comparator, coupled to said data register output terminals and to said counting circuit output terminals, said comparator having a comparator output terminal coupled to an input of said logic array, said comparator responsive to a match between said plurality of stored bits and said count value signals to assert a signal on said comparator output terminal, wherein said logic array is responsive to assertion of said signal on said comparator output terminal to assert said telemetry out signal.

27. A telemetry system in accordance with claim 26, further comprising:
- a telemetry driver circuit, having an input coupled to said logic array to receive said telemetry out signal and an output coupled to said antenna, said telemetry driver circuit responsive to assertion of said telemetry out signal to deliver a pulse to said antenna such that a radio-frequency burst is transmitted.

* * * * *

UNITED STATES PATENT AND TRADEMARK OFFICE
CERTIFICATE OF CORRECTION

PATENT NO. : 5,350,411  Page 1 of 3
DATED : SEPTEMBER 27, 1994
INVENTOR(S) : RYAN ET AL.

It is certified that error appears in the above-indentified patent and that said Letters Patent is hereby corrected as shown below:

Abstract, line 17, delete "tier" and insert in its place --for--.

Column 8, line 65, delete Mealtronic", and insert in its place --Medtronic--.

Column 9, line 56, delete "$T_c$" and insert in its place --$T_e$--.

Column 11, line 8, delete "ØR", and insert in its place --OR--

Column 12, line 11, delete TO, and insert in its place --TØ--.

Column 12, line 60, delete TO, and insert in its place --TØ--.

Column 13, line 9, before "trailing-edge", add --counter value after each time counter 134 has been enabled and then disabled reflects this--.

Column 15, line 22, delete "TS", and insert in its place --T8--.

Column 16, line 58, delete "0.010", and insert in its place --0010--.

Column 17, line 42, delete "dam", and insert in its place --data--.

Column 18, line 24, delete "signal s", and insert in its place --signals--.

Column 22, line 66, delete "(2-39)", and insert in its place --(24-39)--.

Column 23, line 46, delete "$\leq$ 5", and insert in its place --= 5--.

UNITED STATES PATENT AND TRADEMARK OFFICE
CERTIFICATE OF CORRECTION

PATENT NO. : 5,350,411          Page 2 of 3
DATED : SEPTEMBER 27, 1994
INVENTOR(S) : RYAN ET AL.

It is certified that error appears in the above-indentified patent and that said Letters Patent is hereby corrected as shown below:

Column 28,

In Table 4, Transition No. 400, under MATCH, delete "1", and insert in its place --X--.

In Table 4, Transition No. 440, under PLARF, insert—1—.

Table 4, Transition No. 400, under ST3, delete "X7 X" and insert in its place --X--.

In Table 4, Transition No. 466, under PLARF, insert --0--.

In Col. 29, second occurence of Transition No. 400, delete "400", and insert in its place --440--.

In Col. 29/30, Table 4, under STATE NO., delete "TO4", and insert --ST04--.

In Col. 29/30, Table 4, under STATE NO., delete "TO3", and insert --ST03--.

In Col. 29/30, Table 4, under STATE NO., delete "TO2", and insert --ST02--.

UNITED STATES PATENT AND TRADEMARK OFFICE
CERTIFICATE OF CORRECTION

PATENT NO. : 5,350,411
DATED : SEPTEMBER 27, 1994
INVENTOR(S) : RYAN ET AL.

It is certified that error appears in the above-indentified patent and that said Letters Patent is hereby corrected as shown below:

In Col. 29/30, Table 4, under STATE NO., delete "TO1", and insert --ST01--.

In Col. 29/30, Table 4, under STATE NO., delete "TO0", and inset --ST00--.

In Column 42, line 3, after "of", insert --output--.

Signed and Sealed this

Fifth Day of December, 1995

BRUCE LEHMAN

Attest:

Attesting Officer

Commissioner of Patents and Trademarks